(12) United States Patent
Liu et al.

(10) Patent No.: US 8,637,013 B2
(45) Date of Patent: Jan. 28, 2014

(54) TREATMENT OF DRUG-RELATED SIDE EFFECT AND TISSUE DAMAGE BY TARGETING THE CD24-HMGB1-SIGLEC10 AXIS

(75) Inventors: Yang Liu, Ann Arbor, MI (US); Pan Zheng, Ann Arbor, MI (US); Guo-Yun Chen, Ann Arbor, MI (US); Xincheng Zheng, Ann Arbor, MI (US); Xi Cheng, Woodland, CA (US); Steve Kunkel, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 13/426,392

(22) Filed: Mar. 21, 2012

(65) Prior Publication Data
US 2012/0201819 A1    Aug. 9, 2012

Related U.S. Application Data

(62) Division of application No. 12/716,842, filed on Mar. 3, 2010, now Pat. No. 8,163,281.

(60) Provisional application No. 61/157,423, filed on Mar. 4, 2009.

(51) Int. Cl.
*A61K 39/395* (2006.01)
*A61K 39/00* (2006.01)
*A61K 38/16* (2006.01)

(52) U.S. Cl.
USPC ............ 424/130.1; 424/143.1; 424/184.1; 424/185.1; 514/21.2

(58) Field of Classification Search
None
See application file for complete search history.

(56) References Cited

U.S. PATENT DOCUMENTS

| | | | | |
|---|---|---|---|---|
| 6,066,323 | A | * | 5/2000 | Cross et al. ............... 424/158.1 |
| 2004/0248825 | A1 | * | 12/2004 | McCullers .................... 514/43 |
| 2006/0241063 | A1 | * | 10/2006 | Broadhurst .................... 514/43 |

OTHER PUBLICATIONS

Cross et al. "Recruitment of Murine Neutrophils in vivo through endogenous sialidase activity" J.B.C., 6(7), 278, 2003, 4112-4120.*
Varki, Ajit "Natural ligands for CD33-related Siglecs?" Glycobiology, 19(8), 2009, 810-812.*
Oncolmmune Inc. Datasheet: O10002, pp. 1-2.*

* cited by examiner

*Primary Examiner* — Daniel E Kolker
*Assistant Examiner* — James Rogers
(74) *Attorney, Agent, or Firm* — Harness, Dickey & Pierce, P.L.C.

(57) ABSTRACT

The present technology provides methods and compositions for the treatment of tissue-damage related immune dysregulation by administering a composition comprising one or more of CD24; CD24 fragments, variants and derivatives, CD24Fc fusion proteins; HMBG1-binding proteins, binding proteins to HMBG1 Box B; antagonists of HMGB1, polyclonal, monoclonal, recombinant, chimeric, humanized scFv antibodies and antibody fragments to HMGB1 or fragments of HMGB1 and antibodies that bind and suppress the activity of HMGB1 Box B; Siglec 10 agonists such as anti-Siglec 10 antibodies; and combinations thereof to a patient.

8 Claims, 29 Drawing Sheets

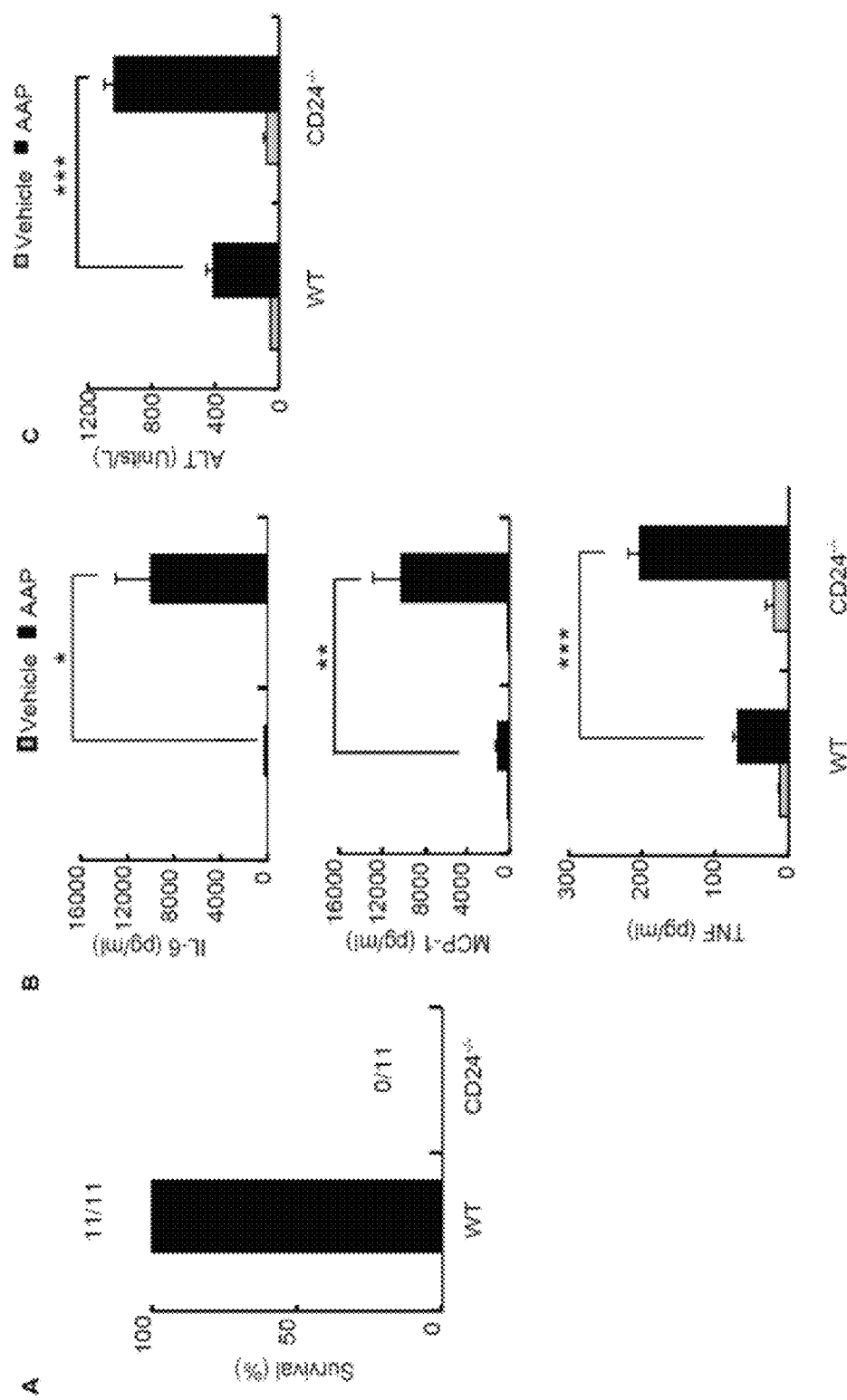
FIG. 1A-C

D
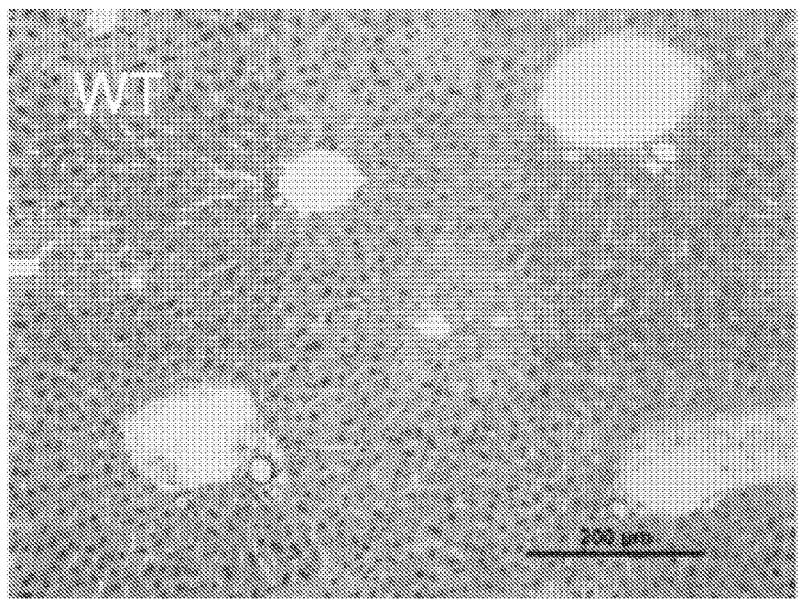
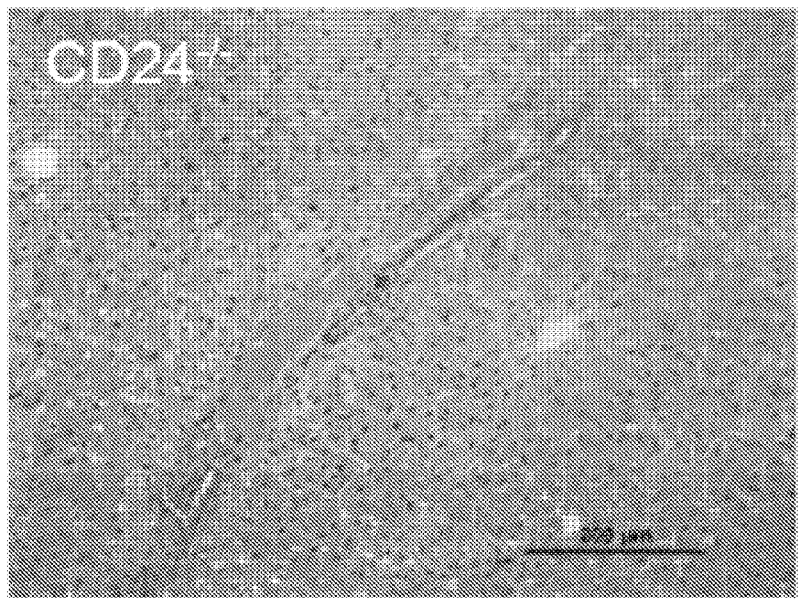
FIG. 1D

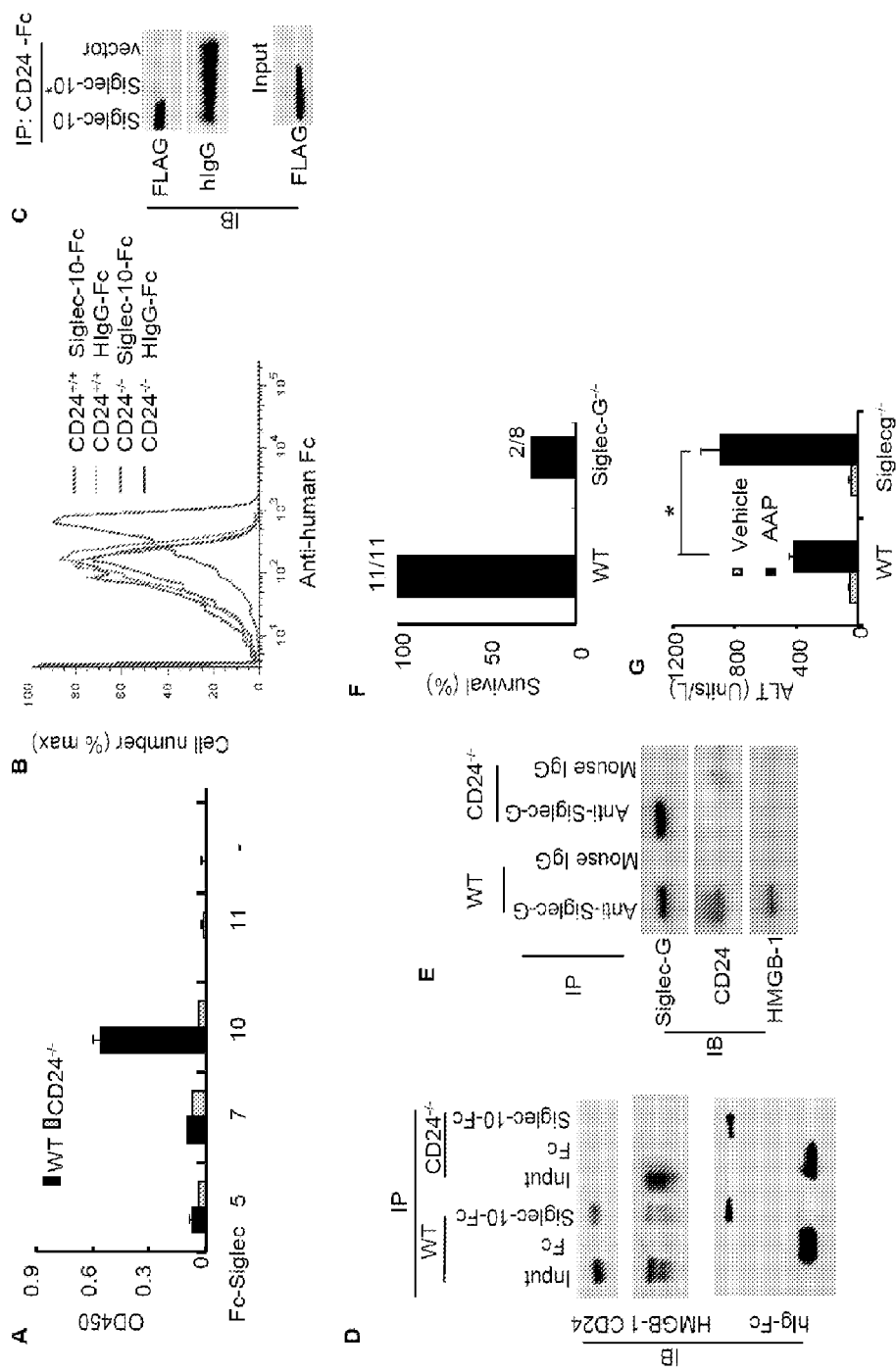
FIG. 3A-G

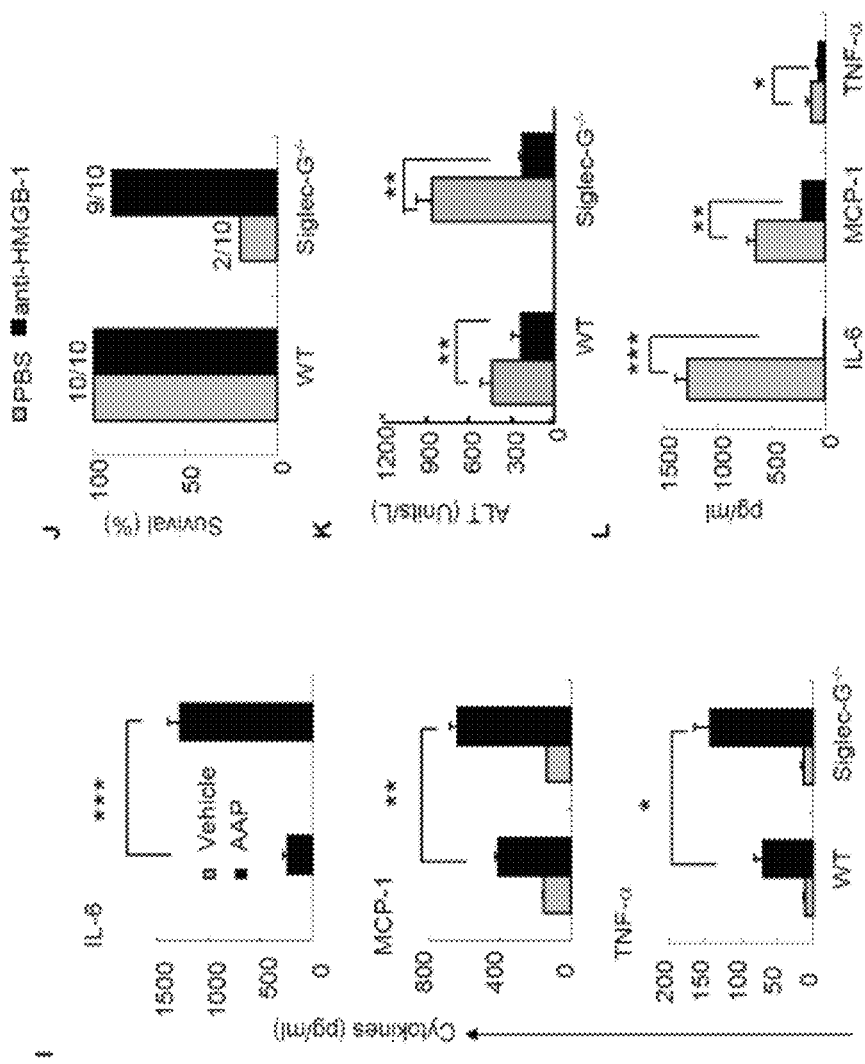
FIG. 3I-L

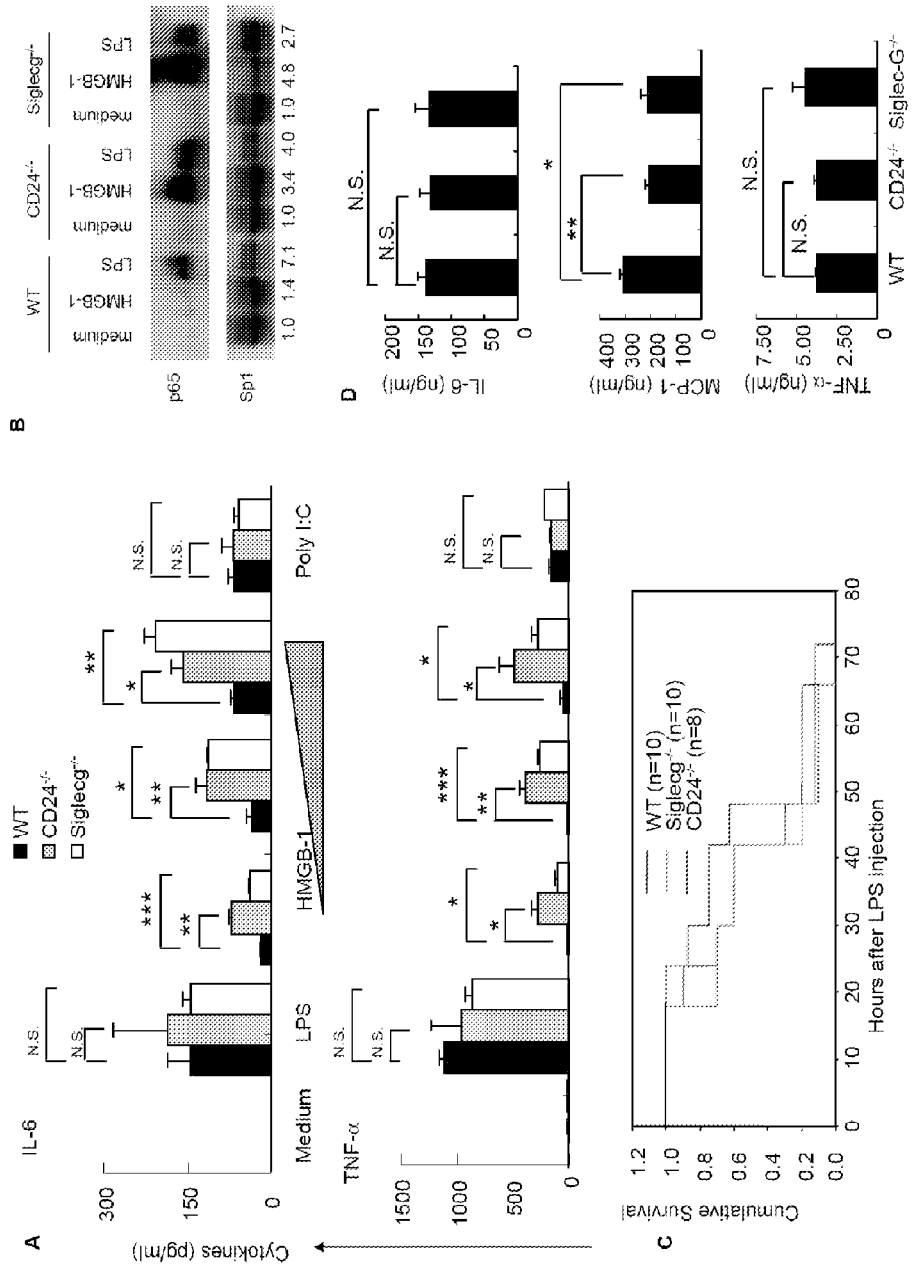
FIG. 4A-D

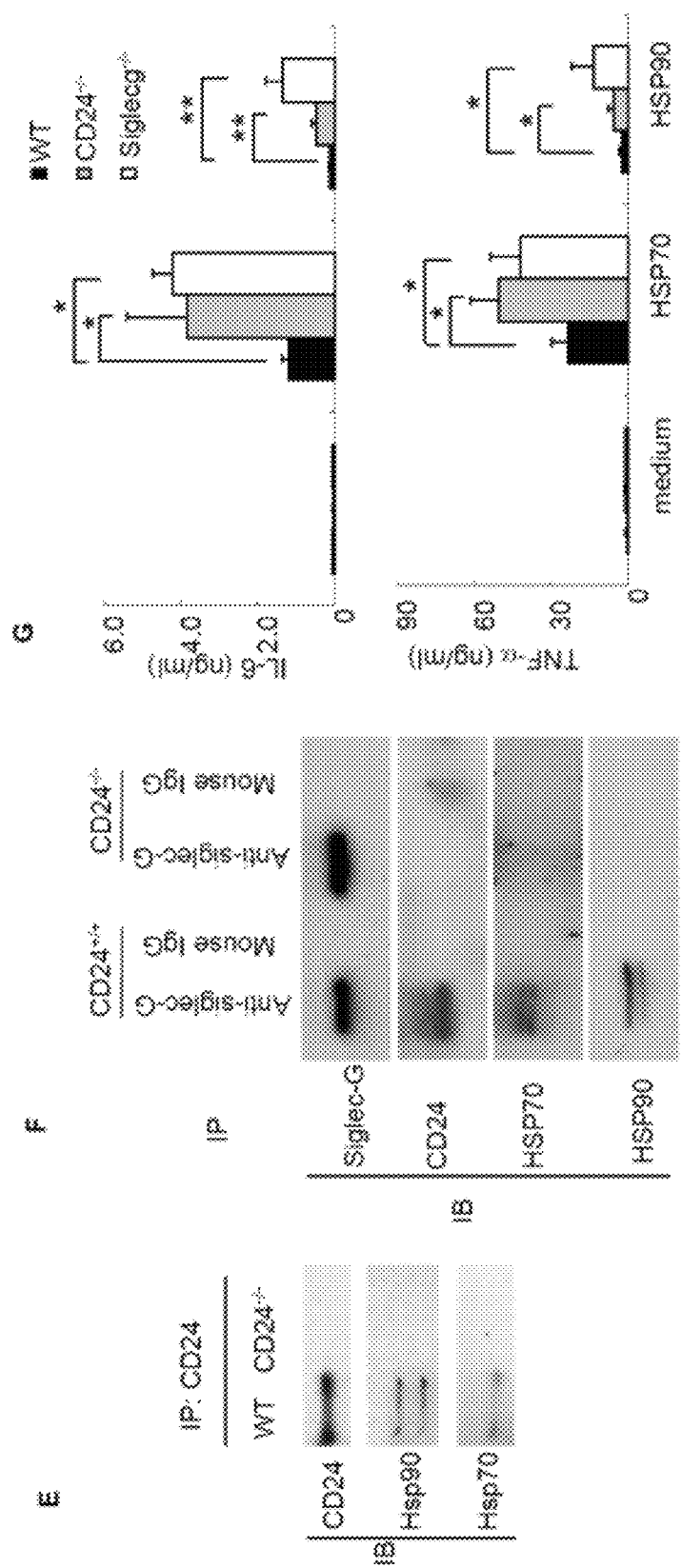
FIG. 4E-G

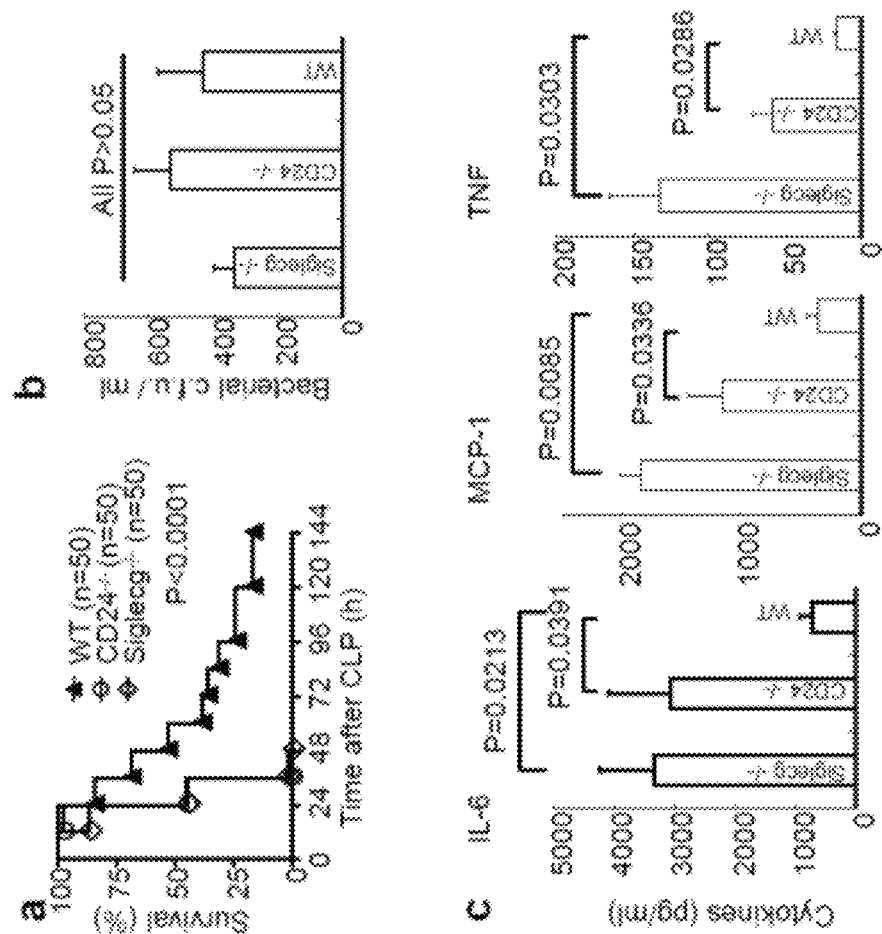
FIG. 10A.-C

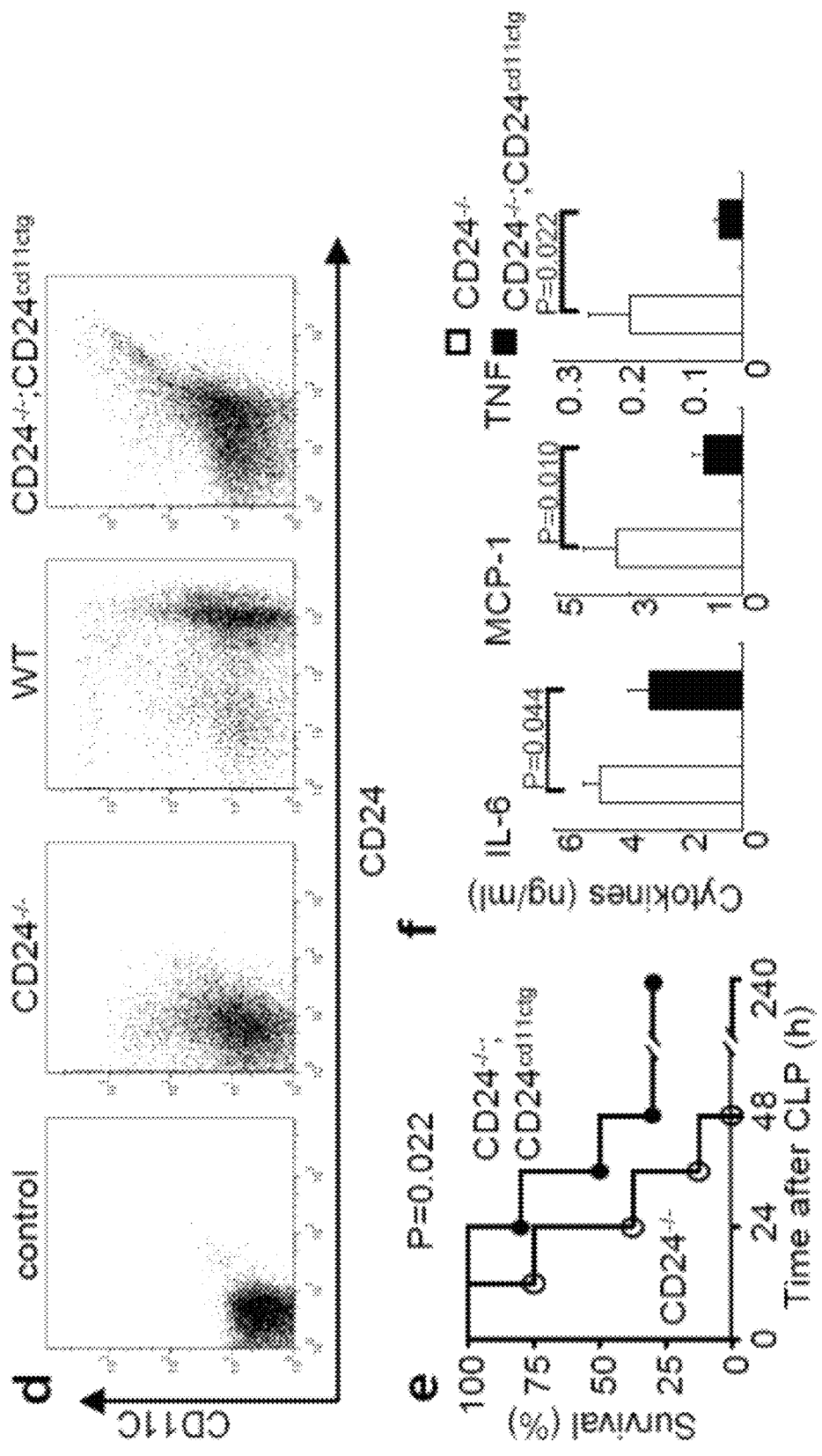
FIG. 10D-F

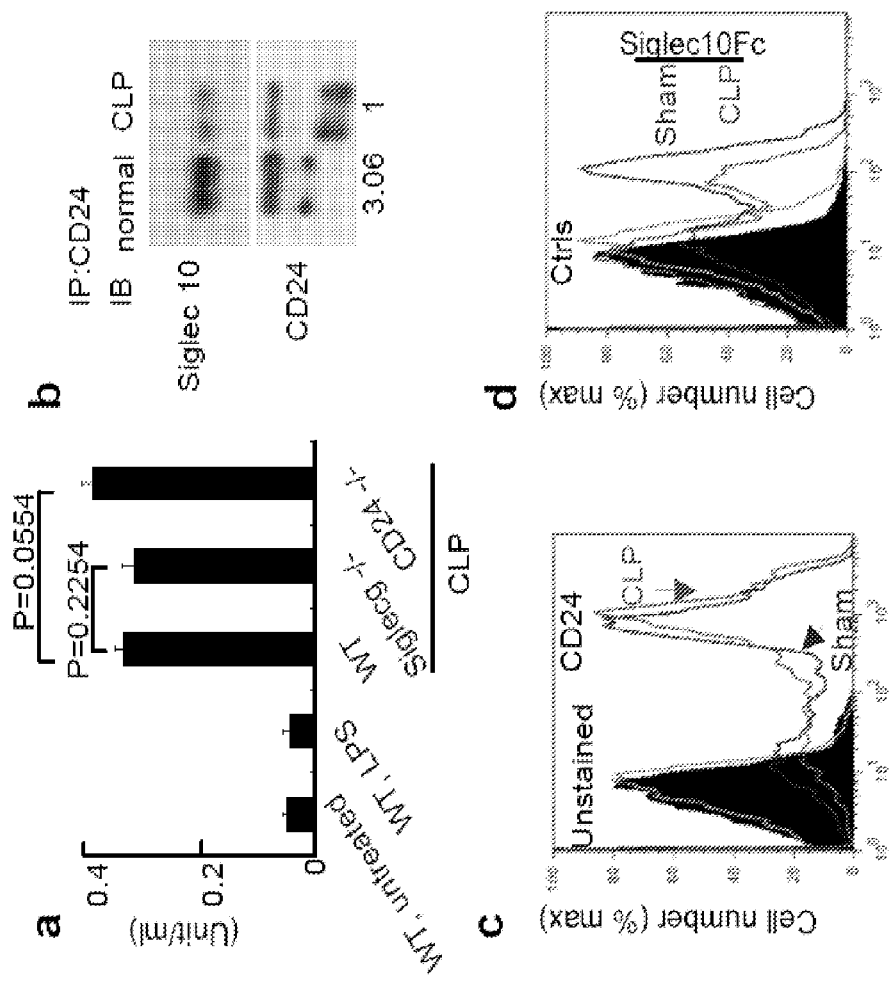
FIG. 12A-D

SEQUENCE LISTING

```
<160> NUMBER OF SEQ ID NOS: 9

<210> SEQ ID NO 1
<211> LENGTH: 8
<212> TYPE: PRT
<213> ORGANISM: Mus musculus
<220> FEATURE:
<221> NAME/KEY: MISC_FEATURE
<223> OTHER INFORMATION: amino acids 57-64 of high mobility group 1
      protein (HMGB1)

<400> SEQUENCE: 1

Gly Lys Phe Glu Asp Met Ala Lys
1               5

<210> SEQ ID NO 2
<211> LENGTH: 9
<212> TYPE: PRT
<213> ORGANISM: Mus musculus
<220> FEATURE:
<221> NAME/KEY: MISC_FEATURE
<223> OTHER INFORMATION: amino acids 154-162 of high mobility group 1
      protein (HMGB1)

<400> SEQUENCE: 2

Tyr Glu Lys Asp Ile Ala Ala Tyr Arg
1               5

<210> SEQ ID NO 3
<211> LENGTH: 10
<212> TYPE: PRT
<213> ORGANISM: Mus musculus
<220> FEATURE:
<221> NAME/KEY: MISC_FEATURE
<223> OTHER INFORMATION: amino acids 76-85 of high mobility group 1
      protein (HMGB1)

<400> SEQUENCE: 3

Thr Tyr Ile Pro Pro Lys Gly Glu Thr Lys
1               5                   10

<210> SEQ ID NO 4
<211> LENGTH: 13
<212> TYPE: PRT
<213> ORGANISM: Mus musculus
<220> FEATURE:
<221> NAME/KEY: MISC_FEATURE
<223> OTHER INFORMATION: amino acids 30-42 of high mobility group 1
      protein (HMGB1)
```

```
<400> SEQUENCE: 4

His Pro Asp Ala Ser Val Asn Phe Ser Glu Phe Ser Lys
1               5                   10

<210> SEQ ID NO 5
<211> LENGTH: 13
<212> TYPE: PRT
<213> ORGANISM: Mus musculus
<220> FEATURE:
<221> NAME/KEY: MISC_FEATURE
<223> OTHER INFORMATION: amino acids 114-126 of high mobility group 1
      protein (HMGB1)

<400> SEQUENCE: 5

Gly Glu His Pro Gly Leu Ser Ile Gly Asp Val Ala Lys
1               5                   10

<210> SEQ ID NO 6
<211> LENGTH: 14
<212> TYPE: PRT
<213> ORGANISM: Mus musculus
<220> FEATURE:
<221> NAME/KEY: MISC_FEATURE
<223> OTHER INFORMATION: amino acids 29-42 of high mobility group 1
      protein (HMGB1)

<400> SEQUENCE: 6

Lys His Pro Asp Ala Ser Val Asn Phe Ser Glu Phe Ser Lys
1               5                   10

<210> SEQ ID NO 7
<211> LENGTH: 15
<212> TYPE: PRT
<213> ORGANISM: Mus musculus
<220> FEATURE:
<221> NAME/KEY: MISC_FEATURE
<223> OTHER INFORMATION: amino acids 112-126 of high mobility group 1
      protein (HMGB1)

<400> SEQUENCE: 7

Ile Lys Gly Glu His Pro Gly Leu Ser Ile Gly Asp Val Ala Lys
1               5                   10                  15

<210> SEQ ID NO 8
<211> LENGTH: 18
<212> TYPE: PRT
<213> ORGANISM: Mus musculus
<220> FEATURE:
<221> NAME/KEY: MISC_FEATURE
<223> OTHER INFORMATION: amino acids 128-145 of high mobility group 1
      protein (HMGB1)

<400> SEQUENCE: 8

Leu Gly Glu Met Trp Asn Asn Thr Ala Ala Asp Asp Lys Gln Pro Tyr
1               5                   10                  15

Glu Lys

<210> SEQ ID NO 9
<211> LENGTH: 19
<212> TYPE: PRT
<213> ORGANISM: Mus musculus
<220> FEATURE:
<221> NAME/KEY: MISC_FEATURE
<223> OTHER INFORMATION: amino acids 127-145 of high mobility group 1
      protein (HMGB1)
```

<400> SEQUENCE: 9

Lys Leu Gly Glu Met Trp Asn Asn Thr Ala Ala Asp Asp Lys Gln Pro
1               5                   10                  15

Tyr Glu Lys

TREATMENT OF DRUG-RELATED SIDE EFFECT AND TISSUE DAMAGE BY TARGETING THE CD24-HMGB1-SIGLEC10 AXIS

CROSS-REFERENCE TO RELATED APPLICATIONS

This application is a divisional of U.S. patent application Ser. No. 12/716,842, now U.S. Pat. No. 8,163,281 filed on Mar. 3, 2010; and also claims the benefit of U.S. Provisional Application No. 61/157,423, filed on Mar. 4, 2009. The entire disclosures of the above applications are incorporated herein by reference.

GOVERNMENT RIGHTS

This invention was made with government support under AI064350, CA058033 and CA112001 awarded by the National Institutes of Health and W81XWH-08-1-0036 awarded by the Army/MRMC. The Government has certain rights in the invention.

FIELD

The present disclosure relates to methods and compositions for the treatment of drug-related side effects and tissue damage by targeting the CD24-HMGB1-Siglec10 axis.

INTRODUCTION

Inflammation is a critical determinant of pathogen virulence in some of the most challenging infectious diseases. Pathogen-associated and danger-associated molecular patterns are two well-known inducers of inflammation. Pathogen-associated molecular patterns (PAMPs) interact with receptors on innate immune cells to initiate protective immune responses. Danger-associated molecular patterns (DAMPs), which are intracellular components such as high mobility group 1 protein (HMGB1), heat shock proteins (HSP) HSP70 and HSP90, and cellular RNA released during cellular injury, also induce TLR-dependent inflammatory responses. Pattern recognition receptors, which recognize pathogens or components of injured cells (danger), trigger activation of the innate immune system.

Despite availability of antibiotics, the mortality and hospitalization of severe sepsis increased rapidly between 1993 and 2003, causing approximately 200,000 annual deaths in the United States alone; see V. Y. Dombrovskiy, A. A. Martin, J. Sunderram, H. L. Paz, Crit. Care Med 35, 1244 (May, 2007). Inability to control the disease highlights a major gap in understanding the root-cause of inflammation associated with infections. Among the best defined causes of inflammation are the PAMPs that interact with pattern-recognition receptors, such as the toll-like receptors (TLR) and Nod-like receptors (NLR). However, PAMPs alone do not appear to satisfactorily explain why antibiotics are ineffective in treating sepsis as PAMPs should be eliminated along with infection. Another source of inflammation is the DAMPs, mostly the conserved intracellular structures exposed after cell deaths, including necrosis or secondary necrosis following apoptosis.

SUMMARY

The present technology provides methods and compositions for the treatment of tissue damage related immune dysregulation by administering a composition comprising one or more of a CD24 agonist; CD24; CD24 fragments, variants and derivatives, CD24Fc fusion proteins; Siglec-10 agonist, such as anti-Siglec 10 antibodies; HMBG1-binding proteins, binding proteins to HMBG1 Box B; antagonists of HMGB1 such as antibodies that bind and suppress the activity of HMGB1 Box B; sialidase inhibitors such as Neu5Ac2en and/or Neu5Gc2en and their derivatives; and combinations thereof. The subject of the administering may be a patient having or susceptible to having tissue damage relating to drug-induced toxicity, for example, drug overdoses, alcoholism, alcohol poisoning fulminant hepatitis caused by drugs, or other types of aseptic tissue injuries including vascular ischemia, liver ischemia and reperfusion, heart ischemia and reperfusion, atherosclerosis, myocardial infarction, stroke, heart failure, surgeries that result in tissue damage, and angina, or septic tissue injuries caused by pathogenic infection such as bacterial infection, sepsis, fulminant hepatitis caused by viral infection, viral or bacterial pneumonia.

In some embodiments, a method for treating inflammation from danger-associated molecular patterns in a subject comprises administering to the subject at least one of: (a) CD24 agonist; (b) Siglec-10 agonist; and (c) a molecule that binds High Mobility Group Box 1 (HMGB1) protein. In some cases, any two of (a), (b), and (c) are administered and in some cases all three of (a), (b), and (c) are administered.

In some embodiments, a method for treating inflammation from septic injuries comprises administering to the subject at least one of: (a) CD24 agonist; (b) Siglec-10 agonist; and (c) a sialidase inhibitor. In some cases, any two of (a), (b), and (c) are administered and in some cases all three of (a), (b), and (c) are administered.

In some embodiments, a method for treating inflammation from danger-associated molecular patterns comprises administering to the subject at least one of: (a) CD24 agonist; (b) Siglec-10 agonist; (c) a molecule that binds High Mobility Group Box 1 (HMGB1) protein; and (d) a sialidase inhibitor. In some cases, any two of (a), (b), (c), and (d) are administered, in some cases any three of (a), (b), (c), and (d) are administered, and in some cases all four of (a), (b), (c), and (d) are administered.

The present technology can also be combined with administration of an immunosuppressive agent.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 shows that CD24 negatively regulates the immune response to AAP-induced liver injury. $CD24^{-/-}$ mice or WT mice were treated with AAP (10 mg/mouse, dissolved in $H_2O$) or vehicle control. Panel A is graphical representation of the survival of mice 20 hours after treatment. Numbers on graph indicate the number of viable over total mice used per group. All WT mice remained healthy. Panel B is graphical representation of serum levels of IL-6, MCP-1 and TNF-α at 6 hours after AAP injection (mean±SD, n=5; *P<0.02, P<0.009; *P<0.002, student t-test). Panel C is graphical representation of ALT levels measured at 6 hours after treatment (mean±SD, n=5; ***P<0.00004, student t-test). Data shown in Panels B and Panel C have been repeated 2 times. Panel D are microphotographs of livers which were isolated at 9 hours after treatment. Representative images (20×) of H&E staining are shown (n=3).

FIG. 2 shows that CD24 associates with, and negatively regulates the immune response to HMGB1. Panel A is a photograph of CD24-associated proteins identified by co-immunoprecipitation. Silver-staining of the SDS-PAGE gel is shown. Arrows indicate the positions of HMGB1 and nucleolin, two abundant CD24-associated DAMP molecules. NS: proteins that coimmunoprecipitated with CD24 non-specifically. Panel B is a photograph of a western blot showing CD24-HMGB1 association of EDTA-disassociated proteins. Panel C is a photomicrograph of a western blot illustrating reciprocal immunoprecipitations of CD24 and HMGB1 were performed with splenocyte lysates isolated from WT mice. Panel D is a photograph of a western blot illustrating direct, cation-dependent interaction between CD24 and HMGB1. Co-immunoprecipitation of recombinant HMGB1 protein with CD24-Fc fusion protein or control IgG-Fc. The requirement for cations was confirmed by disruption of the complex with EDTA. This experiment has been repeated 3 times. Panel E is graphical representation of the survival of mice versus treatment of mice having received i.v. injections with either vehicle (PBS) or mouse HMGB1 mAb (clone 3B1, 150 µg/mouse) 30 minutes prior to i.p. injection of AAP. Composite data from two independent experiments are shown (n=8). Panel F is graphical representation of serum ALT levels at 6 hours after treatment with AAP and HMGB1 antibodies (mean±SD, n=5, **$P<0.005$). Panel G is graphical representation of serum cytokine levels at 6 hours after treatment with AAP and HMGB1 antibodies (mean±SD, n=5, *P, 0.03, **$P<0.004$). Samples in Panels F and G represent two independent experiments, the statistical significance determined by student t-test.

FIG. 3 shows that the Siglec 10/G-CD24-HMGB1 axis negatively regulates immune responses to AAP-induced liver injury. Panel A is graphical representation of the relationship between optical density and the interaction between CD24 and Siglec-Fc fusion proteins. Data shown are optical density and have been repeated 3 times. Panel B is a flow cytometric chromatogram of CD24 interaction with Siglec-10. Representative histograms of two independent experiments are shown. Panel C is a photograph of a western blot of FLAG and hIgG immunoprecipitated proteins COS cells were transfected with FLAG-tagged WT or mutant (*,R119A) Siglec-10 cDNA or a vector control. Communoprecipitations were performed 48 hours later. Panel D is a photograph of western blots illustrating lysates from WT or CD24$^{-/-}$ splenocytes were used to coimmunoprecipitate Siglec-10-Fc, CD24 and HMGB1. Panel E depicts a photograph of a western blot of lysates from WT and CD24$^{-/-}$ spleen cells were precipitated with either Siglec-G antibodies or control mouse Ig. The precipitates were probed with Siglec-G antisera and mAbs specific for CD24 and HMGB1. Panel F is graphical representation of percent survival 20 hours after AAP treatment. Numbers on graph represent the number of surviving mice over total mice used. Panel G is graphical representation of ALT release in serum 6 hours after AAP treatment (mean±SD, *$P<0.005$, n=5). Panel H is a photomicrograph of 20× images of H&E staining of livers harvested 6 hours after AAP injection. Panel I is a graphical representation of cytokine production in blood measured 6 hours after AAP treatment (mean±SD, n=5. *$P<0.05$, $P<0.009$, *$P<0.002$). Panel J is a graphical representation of survival of WT and Siglecg$^{-/-}$ mice 20 hours after treatment. Panel K is graphical representation of ALT release in the blood 6 hours after treatment (mean±SD, n=5, *$P<0.006$). Panel L is graphical representation of cytokine release in the blood 6 hours after treatment (mean±SD, n=5, *$P<0.03$, $P<0.0006$, *$P<0.0004$). Panels K-L are representative of two independent experiments. Statistical significance was determined by the student's t-test.

FIG. 4 shows CD24 and Siglec-G negatively regulate immune responses to HMGB1, HSP70 and HSP90, but not to LPS and poly I:C. Panel A is graphical representation of the production of cytokines by DCs. DCs cultured from WT, CD24-/- or Siglecg-/- bone marrow were stimulated with LPS (100 ng/ml), polyI:C (10 µg/ml) or increasing doses (5, 10 and 20 µg/ml) of HMGB1 for 6 hours, the supernatants were analyzed for the levels of inflammatory cytokines, using cytokine beads array. Data represents the mean±SD for three independent cultures of DCs in each genotype and have been repeated at least three times. Panel B is a photograph of a western blot of p65 and Sp1 in various cell lysates. BMDCs isolated from WT, CD24-/- or Siglecg-/- mice were stimulated under the indicated conditions for 6 hours. The nuclear lysates were prepared and the activation of NF-κB was assessed by blotting for the p65 subunit of NF-κB. The loading of nuclear protein was determined by amounts of Sp1 protein. Fold induction over medium control are provided underneath the photograph. Data are representative of two independent experiments. Panel C is graphical representation of Kaplan Meier survival plots of age-matched male mice received i.p. injections of LPS (450 µg/mouse). No statistical significance was found by log-rank tests. Panel D is a graphical representation of cytokine production in the serum 4 hours after LPS injection (mean±SD, the statistical significance of the differences between the control and one of the treated groups were determined by student t-test. *$P<0.03$, **$P<0.002$). The numbers of mice used are the same as Panel C. Panel E is a photograph of a western blot for the presence of CD24, Hsp90 and Hsp70 in co-immunoprecipitation experiments of CD24 and Hsp70 and Hsp90. Panel F is a photograph depicting a western blot of Siglec-G, CD24, Hsp70 and Hsp90. Siglec-G associates with Hsp70 and Hsp90 through CD24. The same precipitates used in FIG. 3 Panel E were analyzed for Hsp70 and Hsp90 by immunoblot. Panel G is a graphical representation of cytokines IL-6 and TNF-α production in WT, CD24$^{-/-}$ and Siglecg$^{-/-}$ null mice. Deficiencies in CD24 and Siglec-G enhanced production of IL-6 and TNF-α at 6 hours after stimulation with HSP70 and HSP90. Data shown represent the mean±SD of cytokines from 4 independent isolates of DCs from each genotype and have been repeated twice.

FIG. 5 is a graphical representation of the production of various serum cytokines in CD24Fc and Human IgFc control mice showing that CD24Fc offers protection from AAP mediated liver injury. WT mice received injection of AAP (16 mg/mouse, dissolved in H$_2$0) in conjunction with either CD24Fc or control IgG Fc. Serum was collected 5 hours after AAP injection and cytokines and ALT were measured by multiple cytokine beads array. Data shown are serum levels of IL-6, IL-10, MCP-1, IFN-γ and TNF-α at 5 hours after AAP injection (mean±SE, n=5; *$P<0.05$ and **$P<0.01$, student t-test).

FIG. 6 shows the characterization of anti-HMGB-1 mAbs used. Panel (a) is an immunoblot showing the interaction of 3E8 and 3B1 with recombinant HMGB-1 obtained from R&D system. Note that while 3E8 also binds to a truncated HMGB-1 in the preparation, 3B1 only recognize the full length form from the same preparation. Surface Plasmon Resonance (SPR) using the BIACORE3000 revealed that Kd for 3B1-HMGB-1 interaction is 7.8 nM, while that for 3E8-

HMGB-1 interaction is 1.3 nM. Panel (b) shows inhibition of TNFα production from CD24−/− dendritic cells, stimulated with HMGB-1 (20 μg/ml) in the presence of given amounts of 3B1 or mouse IgG control. Supernatants were harvested after 6 hours of culture and measured by cytokine beads array.

FIG. 7 shows that CD24 does not bind to inhibitory Box A of HMGB-1. cDNA encoding FLAG-tagged full-length (F), inhibitory Box A (A) or Box B plus acidic tail (BC) were transfected into COS7 cells. The cells were lysed and precipitated with recombinant CD24Fc. The precipitates were blotted with either anti-FLAG or anti-IgG Fc. The relative amounts of truncated proteins expressed were measured by anti-FLAG. The positions of the truncated products are diagrammed at the top.

FIG. 8 shows characterization of anti-Siglec-G antisera. Siglecg−/− mice that were immunized with WT spleen cells (approximately 107/mouse/injection) that have been stimulated with LPS (10 μg/ml) for 24 hours. After three immunizations, the sera were collected. Panel (A) shows specific binding to WT but not Siglecg−/− spleen cells. Spleen cells were stained with 1:100 dilution of the mouse anti-serum, and the IgG bound to the cells were determined by phycoerythorin-conjugated goat-anti-mouse IgG-Fc. The size of the positive subset roughly matches what was revealed by the GFP markers (3). Panel (B) shows a Western blot that reveals a specific band that reacts to anti-Siglec-G anti-sera (1:100).

FIG. 9 shows that Siglec-10Fc reacts with both Siglecg+/+ and Siglecg−/− spleen cells. Spleen cells from Siglecg+/+ and Siglecg−/− mice were incubated with biotinylated CD24-Fc or Fc control (2 μg/ml). After washing away the unbound proteins, the cell-associated proteins were detected by phycoerythorin-conjugated streptavidin. The FACS stainings have been repeated twice.

FIG. 10 shows targeted mutation of either the Siglecg or the Cd24 gene exacerbates sepsis without increasing bacterial colony forming units (CFU) in the blood. Panel (a) shows survival of WT, Cd24−/−, Siglecg−/− mice. The X-axis show hours after CLP, while the Y-axis show % of live mice. Data shown are summary of five experiments, each involving 10 mice per group. Panel (b) shows bacterial burdens in the blood samples (CFU/ml) harvested at 12 hours after CLP (n=8). Panel (c) shows elevation of inflammatory cytokines in mice with targeted mutation of either Cd24 or Siglecg (n=8). Panels (d)-(f) show dendritic cell-exclusive expression of CD24 conveys protection against sepsis. Panel (d) shows CD24−/− mice that express CD24 under the control of CD11c promoter, CD24−/−; CD24Cd11ctg. Data shown are FACS profiles depicting pattern of CD24 expression in the splenocytes of WT, CD24−/− and CD24−/−; CD24Cd11ctg mice. Similar patterns were observed in the lymph node cells. Panel (e) shows expression of CD24 on DC increased mouse survival after CLP. CD24−/−; CD24cd11ctg mice (n=10) and their CD24−/− (n=8) littermates were treated by CLP and monitored for their survival. Panel (f) shows CD24 expression on DC suppressed production of inflammatory cytokines (n=11). All data presented were repeated at least three times.

FIG. 11 shows that CD24-Siglec 10 interaction depends on sialyation of CD24. In panel (a), biotinylated CD24Fc were pretreated with either control buffer (lane 1) or sialidase from *Streptococcus pneumoniae* (lane 2, specific for α2-3-sialosides), *Clostridium perfringens* (lane 3, active for α2-6- or α2-3-sialosides), or *Vibrio cholerae* (lane 4, 10 active for α2-3-, α2-6- or α2-8-sialosides) overnight at 37° C. The Siglec 10Fc fusion protein was incubated with the digested CD24Fc, and the complex was pulled down with streptavidin beads. The amounts of bead-bound Siglec 10Fc and CD24Fc were determined by Western blot with antibodies specific for either Siglec 10 or CD24. Panel (b) shows efficient inhibition of CD24-Siglec 10 interaction by sialosides. Siglec 10Fc were preincubated with given concentration of either Neu5Acα2-3Lac or Neu5Acα2-6Lac and then added to plate-bound CD24Fc. The CD24-bound Siglec 10Fc were measured by biotinylated anti-Siglec 10 followed by HRP-labeled streptavidin. Panel (c) shows efficiency of desialylation and resialylation, as indicated by their electrophoresis mobility. Panel (d) shows both α2-3- and α2-6-resialylations of CD24 restore Siglec 10Fc binding. The data presented were repeated at least three times.

FIG. 12 shows increased circulating sialidase activity and reduction of Siglec 10 binding of CD24 in CLP mice. Panel (a) shows sialidase activity in the sera of untreated, LPS- or CLP treated mice. Sera were collected at 12 hours after treatment (n=5). Panel (b) shows pretreatment of biotinylated CD24Fc with sera from CLP mice reduced its binding to Siglec 10Fc. Data shown are co-IP with streptavidin-conjugated beads. The top panel shows the amounts of Siglec 10Fc in the precipitates as determined by Western blot. The molecular weight shift of CD24 is demonstrated by Western blot using HRP-labeled streptavidin in the bottom panel. Panel (c) shows that CLP does not affect CD24 expression in spleen cells. Panel (d) shows that CLP significantly reduced spleen cell binding to Siglec 10Fc. Histograms shown on top panels are FACS 11 profiles depicting distribution of CD24 in sham-surgery (blue line) or CLP (red line) spleen cells. The bar graphs in the bottom panels present means+/−S.D. of mean fluorescence intensities from 3 independent experiments. Panel (e) shows CLP alters the molecular weight distribution of CD24 in the spleen cell lysates, as determined by Western blot. All data presented have been repeated at least three times. UT: untreated; US: unstained.

FIG. 13 shows sialidase inhibitors protect mice against sepsis. Panel (a) shows that a mixture of sialidase inhibitors blocks serum sialidase activity. Sera from CLP mice were mixed with given doses of inhibitors, Neu5Ac2en (AC), Neu5Gc2en (GC), or both (AC+GC) prior to the assay. The sialidase activity was measured using the Amplex Red Neuraminidase assay kit. Panel (b) shows sialidase inhibitors prolong survival of mice after CLP (n=10). The mice received a mixture of AC and GC (100 μg/mouse/injection) immediately prior to CLP and every 12 hours thereafter. Panel (c) shows sialidase inhibitors reduce the levels of multiple inflammatory cytokines. Sera were collected at 24 hours after CLP to measure cytokines. Data shown are means+/−S.D. (n=8). Panel (d) shows sialidase inhibitors had no effect on the serum bacterial CFU. Data shown are means+/−S.D. (n=8). Panels (e) and (f) show targeted mutation of Siglecg abrogates protection by sialidase inhibitors. Panel (e) shows survival of CLP mice (n=10). Panel (f) shows production of inflammatory cytokines at 24 hours after CLP. Data shown are means+/−S.D. (n=7). Data from (a)-(d) have been reproduced in 4 independent experiments, while those in (e) and (f) have been reproduced twice.

FIG. 14 shows CD24 expressed on hematopoietic cells conveys protection against sepsis. Lethally irradiated Cd24−/− mice were reconstituted with bone marrow from either WT or CD24−/− mice (KO). Eight weeks later the chimera mice were subject to CLP. Panel (a) shows expression of CD24 in hematopoietic cells increased mouse survival. Panel (b) shows CD24 expressed on hematopoietic cells suppressed production of inflammatory cytokines.

FIG. 15 shows sialidase-desialylation and sialyltransferase-resialylation of CD24-Fc. CD24Fc was desialyated (deSia CD24Fc) with or without resialyation by either α2-6-sialyltransferase (2-6ST CD24Fc) or α2-3-sialyltransferase (2-3ST CD24Fc). The efficiency of the enzymatic reactions was monitored by their binding to biotinylated Maackia Amurensis Lectin I (MAA) (a) or biotinylated *Sambucus Nigra* Lectin (SNA) (b). Data in (a) show that α2-3-resialyation restores binding of deSia CD24Fc to MAA. Our extensive characterization of MAA binding to a large array of glycans indicated that MAA nonspecifically binds to desialyated glycan (data not shown). Interestingly, the nonspecific binding can be prevented by α2-6-resialyation. The untreated CD24Fc showed weak binding to SNA (b, right panel), indicating that it has little α2-6-sialyation. Resialyation substantially increased α2-6-sialyation. Thus, the data in this figure indicate that resialytation of CD24-Fc is specific and efficient.

DETAILED DESCRIPTION

Figure 2:
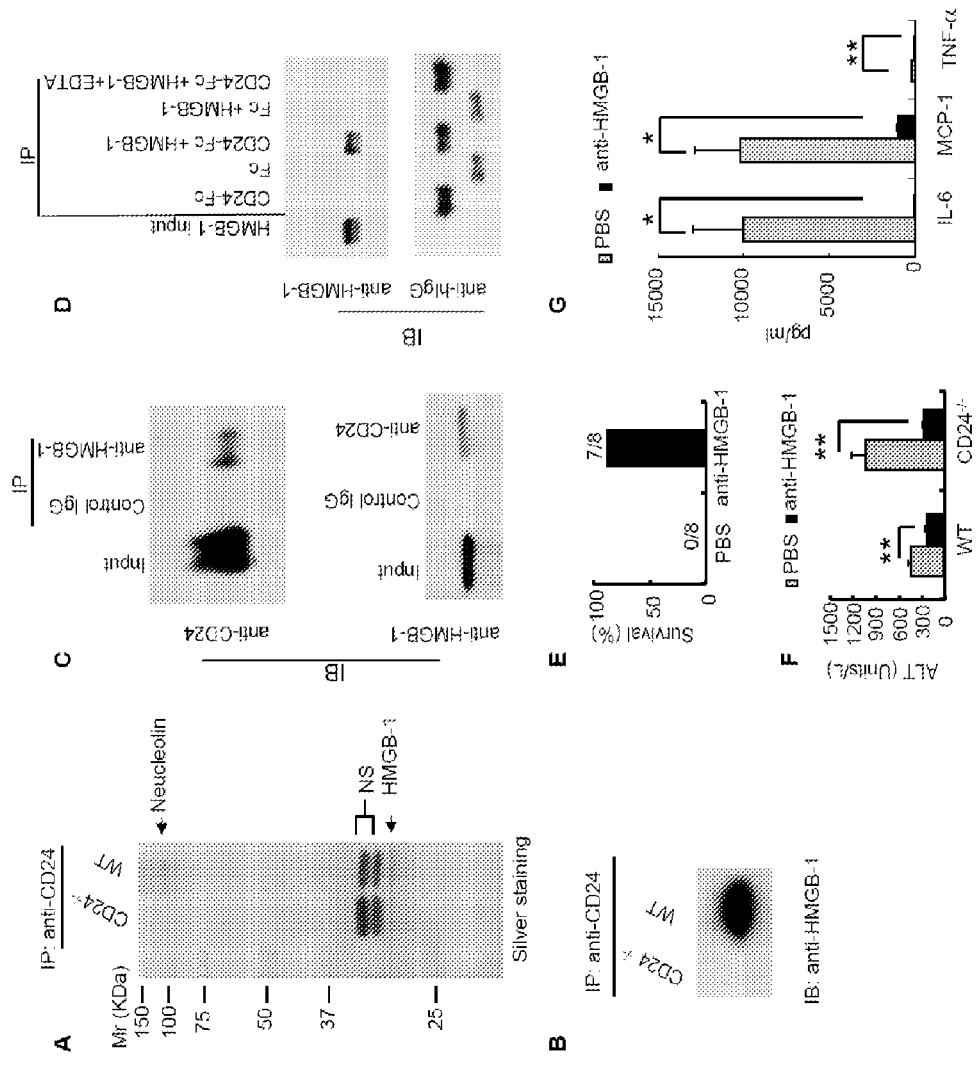

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

The present technology relates to treating inflammation caused by a subject's immune response to damage- and/or pathogen-associated molecular patterns.

Many commonly used drugs such as aspirin, acetaminophen, alcohol and infections cause necrosis of normal cells. The contents of necrotic cells can induce an inflammatory response that can be lethal. The present investigators have identified a pathway, involving CD24 and Siglec 10 that acts as a potent repressor of the inflammatory response. Inflammation and side effects thereof can be effectively treated by either blocking HMGB1 or stimulating CD24 and Siglec 10.

The present investigators have identified that the immunological mediators CD24 and Siglec-10 selectively repress tissue damage-induced immune responses. We report that CD24-deficient mice exhibit increased susceptibility to danger but not pathogen-associated molecular patterns. CD24 associates with high mobility group box 1 (HMGB1), heat shock protein 70 (HSP70) and heat shock protein 90 (HSP90), which negatively regulates their stimulatory activity and inhibits nuclear factor-kappa B (NF-κB) activation. This occurs at least in part through CD24 association with Siglec-10 in humans or Siglec-G in mice. Our results reveal that the CD24-Siglec G (or Siglec-10 in humans) pathway protects the host against a lethal response to pathological cell death and discriminates danger-associated versus pathogen-associated molecular patterns.

An acetaminophen (AAP)-induced liver necrosis model was used to identify genes that regulate the innate immune response resulting from tissue injury. A sublethal dose of AAP (10 mg/mouse), which is tolerated by wild-type (WT) mice, caused rapid death of CD24-deficient mice (CD24$^{-/-}$) mice within 20 hours (FIG. 1 Panel A). We then tested whether CD24 regulated the inflammatory response to AAP-induced liver injury because CD24 is expressed on liver oval cells and hematopoietic cells, but not hepatocytes. Indeed, we detected a massive increase in the inflammatory cytokines interleukin-6 (IL-6), monocyte chemotactic protein-1 (MCP-1) and tumor necrosis factor-alpha (TNF-α) after AAP treatment (FIG. 1 Panel B). This was accompanied by increased amounts of serum alanine transaminase (ALT), which is indicative of liver damage (FIG. 1 Panel C), and liver hemorrhage and necrosis (FIG. 1 Panel D). These observations revealed that CD24 protects against AAP-induced hepatoxicity, most likely by regulating the inflammatory response.

CD24 is a small glycosyl-phosphoinositol-anchored protein that is able to provide costimulatory signals to T cells and has been implicated in the development of autoimmune disease. An object of the present study was to identify proteins that associate with CD24 because none of the known CD24 ligands provided insight into its protective effect in our liver injury model. Proteins whose interactions can be disrupted by the cation chelator, EDTA were focused, because more than 90% of the mass of CD24 is estimated to be derived from glycosylation, and because protein-polysaccharide interactions largely depend on cations. CD24 was immunoprecipitated and its associated proteins from lysates of mouse splenocytes were isolated and purified. The proteins eluted by EDTA were subjected to high throughput mass spectrometry analysis and SDS-PAGE. HMGB1, a prototypical DAMP molecule that activates the immune response following tissue damage, was among the most prominent proteins that we identified (FIG. 2 Panel A and Table 1). HMGB1 coimmunoprecipitated with CD24 and this interaction was specific (FIG. 2 Panel B and C). A recombinant CD24-Fc fusion protein specifically coimmunoprecipitated recombinant HMGB-1, demonstrating that the interaction between CD24 and HMGB-1 was direct (FIG. 2 Panel D).

To determine whether the hypersensitivity to AAP observed in $CD24^{-/-}$ mice was the result of an enhanced immune response to HMGB1, AAP-treated mice were injected with antibodies to HMGB1. In one representative experiment, blockade of HMGB1 rescued 87.5% of the mice that received AAP (FIG. 2 Panel E). Treated mice exhibited decreased ALT abundance, indicating reduced hepatocyte destruction (FIG. 2 Panel F). The production of IL-6, MCP-1 and TNF-α were also greatly reduced (FIG. 2 Panel G). Thus, CD24 protects against AAP-induced lethal hepatoxicity by dampening the immune response against HMGB1.

Figure 7:
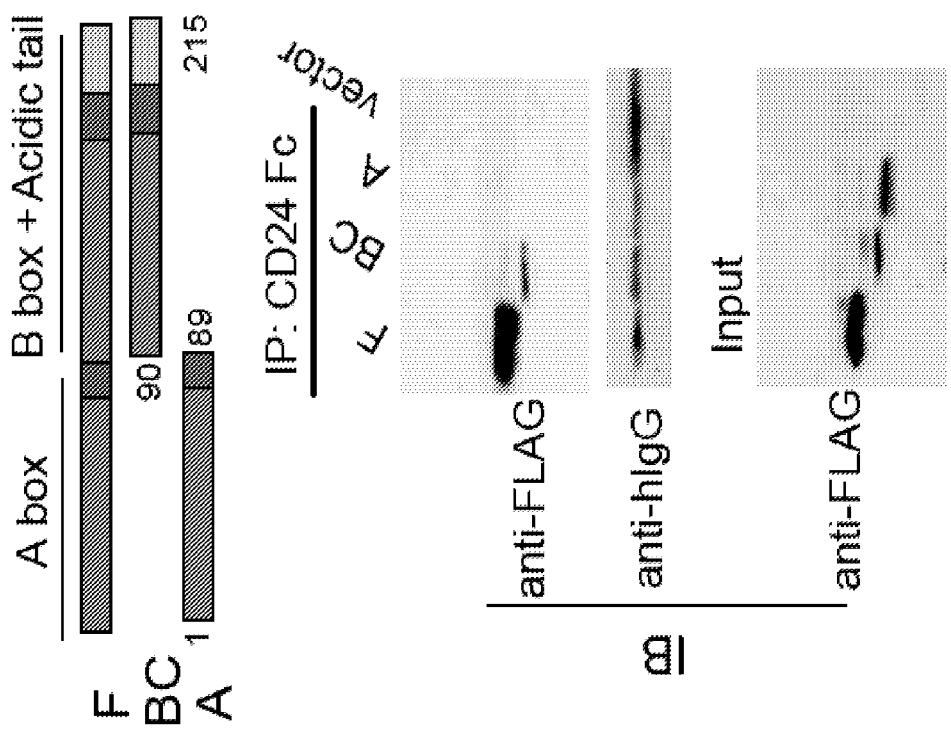

HMGB1 can be divided into two domains: an inhibitory A box and a stimulatory B box. To determine whether CD24 inhibits HMGB1 by binding to the inhibitory A box, deletion mutants were produced lacking either the A box or the B box. CD24-Fc immunoprecipitated full length HMGB1 and the box B-containing mutant, but not the box A-containing mutant (FIG. 7). Thus, inhibition of HMGB1 by CD24 does not require direct interaction with box A.

Figure 3H:
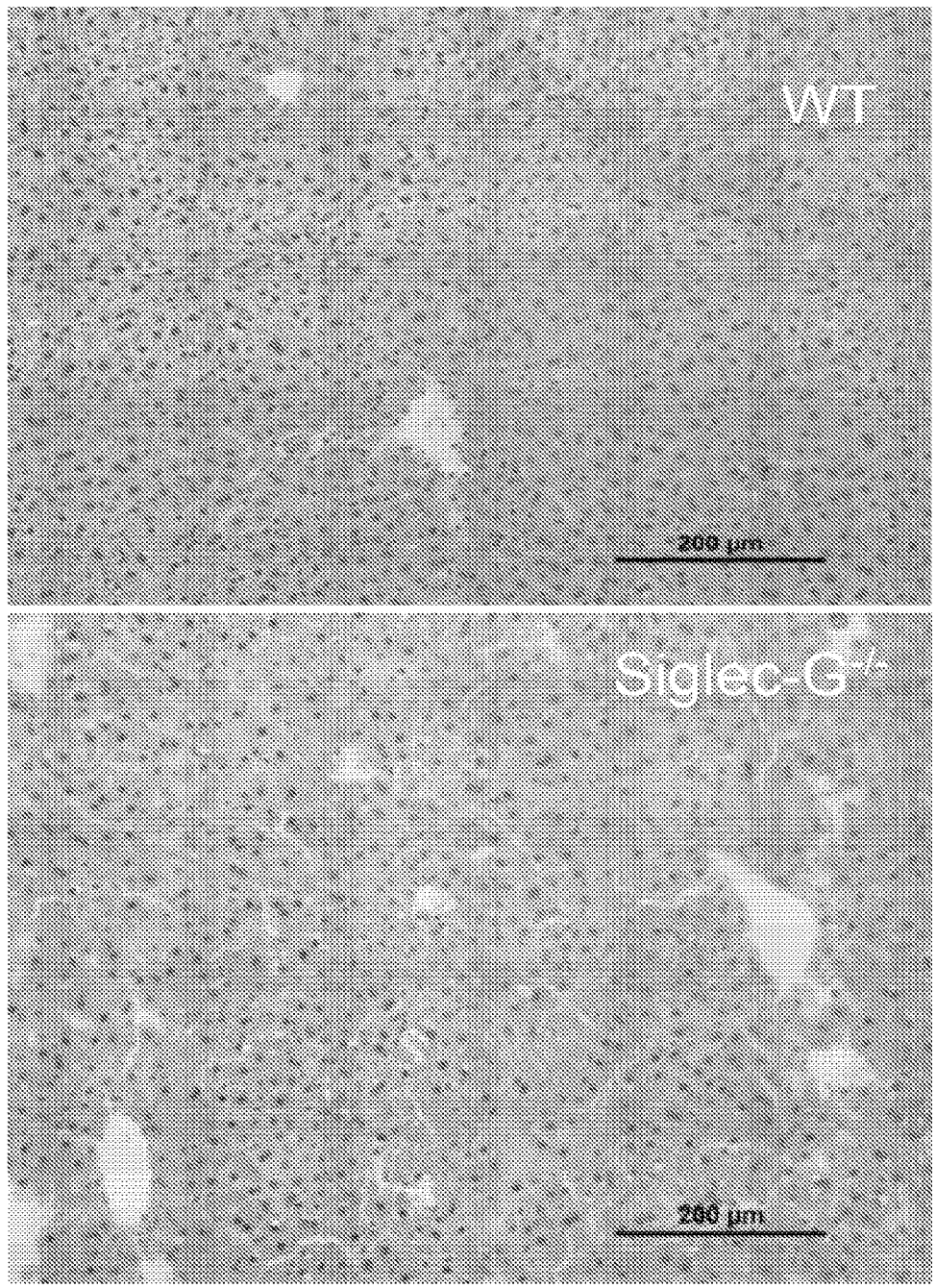

CD24 has no known mechanism for signal transduction. In order to understand how CD24 negatively regulates HMGB1, a potential CD24 receptor was searched that may transduce signals downstream of CD24. Sialic acid-binding Ig-like lectins (Siglecs) were identified as candidates for further study. Siglecs are cell surface receptors of the immunoglobulin super-family that recognize sialic acid-containing proteins. Siglecs are primarily expressed by cells of hematopoietic origin. Most Siglecs are considered to be negative regulators of the immune system because they contain one or more cytosolic immune receptor tyrosine-based inhibitory motifs (ITIMs). To determine whether CD24 interacts with Siglecs, splenocytes were incubated on plates coated with the recombinant extracellular domains of ITIM-containing Siglec-5, -7, -10 or -11. Siglec-10, but not Siglecs-5, -7 or -11, bound to CD24 (FIG. 3A). Flow cytometric analysis indicated that CD24 is the primary receptor for Siglec-10-because WT but not $CD24^{-/-}$ splenocytes showed detectable binding to soluble Siglec-10-Fc (FIG. 3 Panel B). Furthermore, in COS cells, FLAG-tagged Siglec-10 coimmunoprecipitated with Siglec-10-Fc whereas the inactivating R119A mutation of Siglec-10 (analogous to the R97A in sialoadhesin), abrogated the interaction (FIG. 3 Panel C).

Without wishing to be bound by any particular theory, it was believed that CD24, Siglec-10 and HMGB1 might form a tri-molecular complex because CD24 can interact with both HMGB1 and Siglec-10. Indeed, Siglec-10-Fc was able to immunoprecipitate HMGB1 from lysates of WT but not $CD24^{-/-}$ splenocytes (FIG. 3 Panel D), indicating that their interaction was strictly dependent on CD24 expression.

Figure 8:
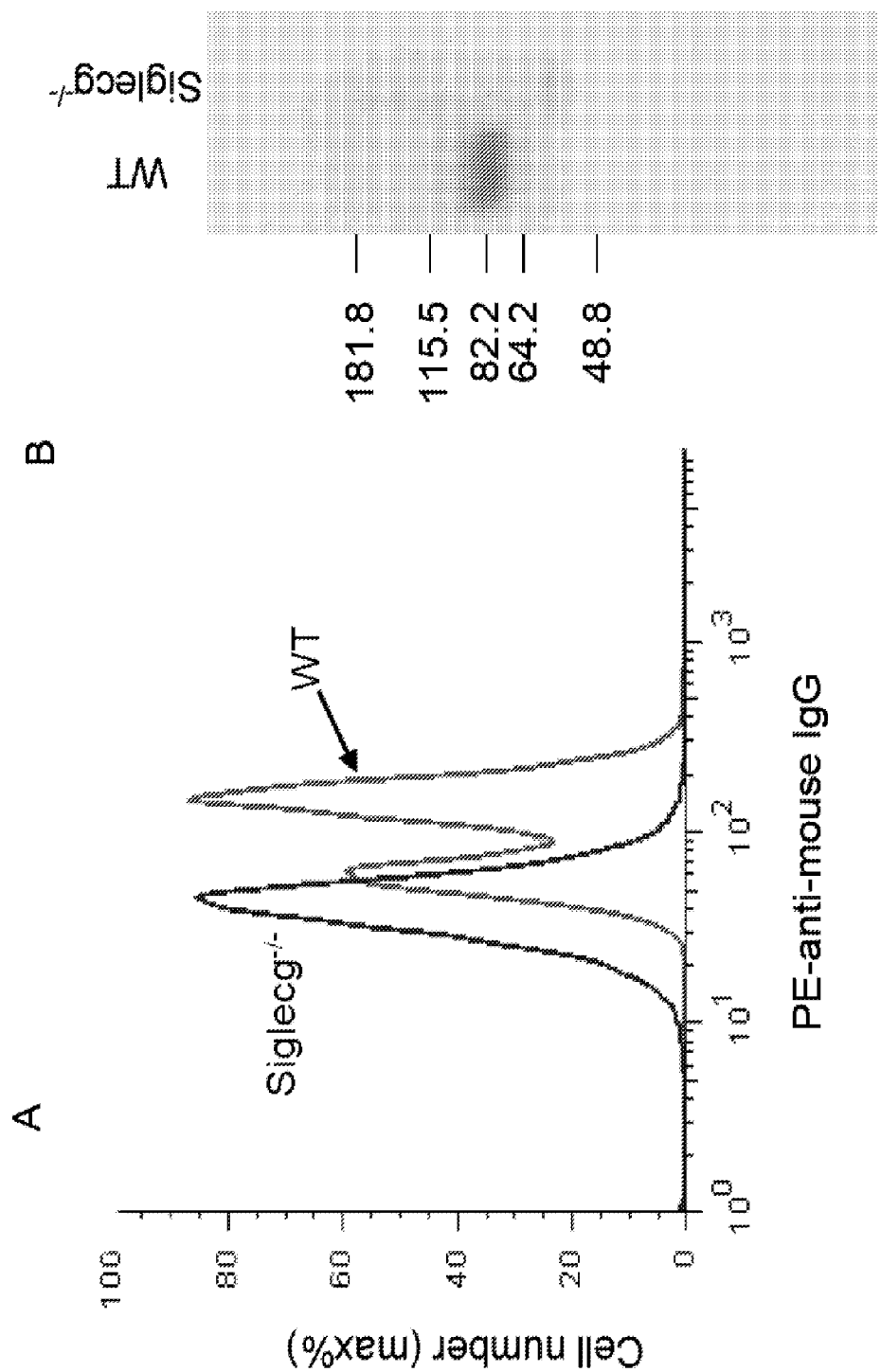
Figure 9:
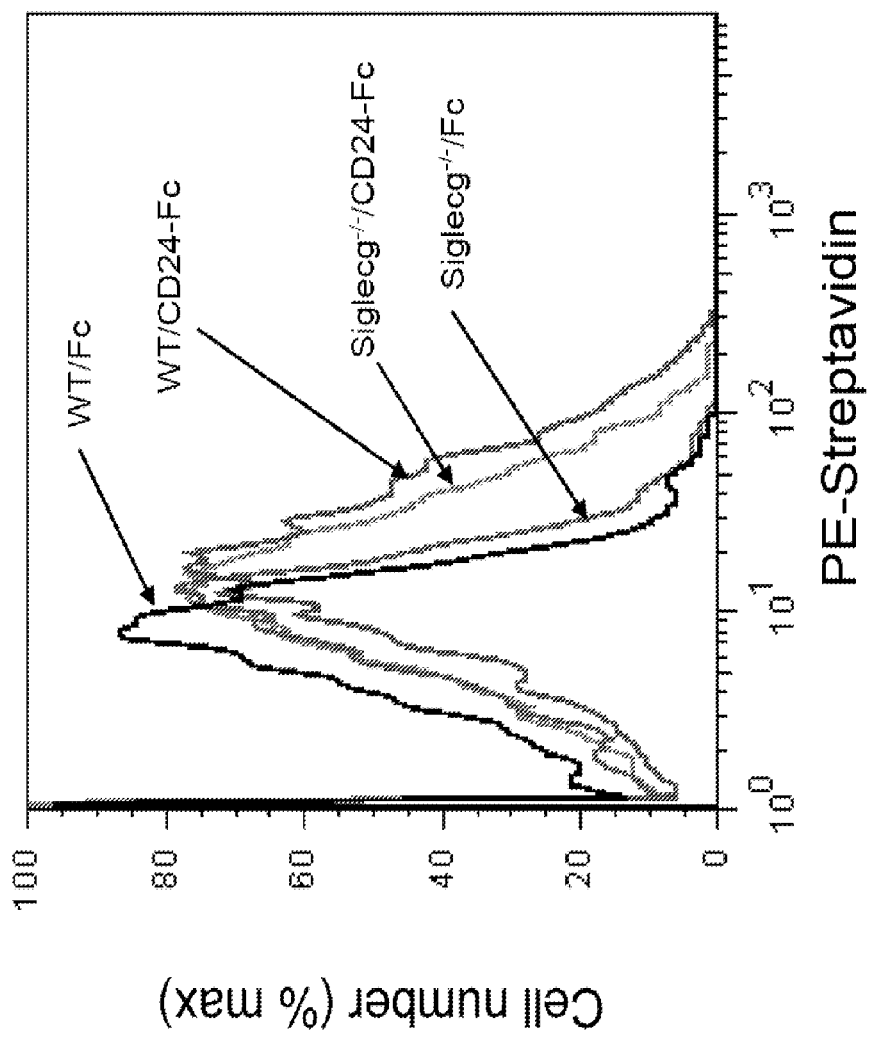

The likely murine homologue of Siglec-10 is Siglec-G. Anti-Siglec-G anti-sera were prepared by immunizing $Siglecg^{-/-}$ mice with WT spleen cells (FIG. 8). Using this antisera, Siglec-G coimmunoprecipitated CD24 (FIG. 3 Panel E). CD24-Fc showed stronger binding to WT splenocytes in comparison to $Siglecg^{-/-}$ splenocytes, indicating that Siglec-G contributed to CD24-Fc binding; however, consistent with previous reports of multiple CD24 receptors, Siglec-G-deficiency did not abrogate CD24-Fc splenocyte binding (FIG. 9). We next determined if the absence of Siglec-G would also convey hypersensitivity to AAP. Indeed, only 25% of $Siglecg^{-/-}$ mice survived a sublethal dose of AAP (FIG. 3 Panel F). The enhanced susceptibility was accompanied by increased release of ALT (FIG. 3 Panel G), liver necrosis and hemorrhage (FIG. 3 Panel H), as well as increased amounts of inflammatory cytokines in the blood (FIG. 3 Panel I). To test whether the enhanced liver toxicity was mediated by HMGB1, $Siglecg^{-/-}$ mice were treated with antibodies to HMGB1. Inhibition of HMGB1 prevented mortality in 90% of AAP-treated $Siglecg^{-/-}$ mice (FIG. 3 Panel K). Serum ALT and inflammatory cytokines) were also largely diminished (FIG. 3 Panel K and Panel L).

It is believed that CD24 and Siglec-10 are unlikely to function by acting directly on hepatocytes because they are not expressed by these cells. Dendritic cells (DCs), however, respond to HMGB1 and express both CD24 and Siglec-G. To test whether DCs can respond to HMGB1, bone marrow-derived DCs isolated from WT, $CD24^{-/-}$ or $Siglecg^{-/-}$ mice we cultured and stimulated with HMGB1 or the TLR ligands LPS or poly I:C. HMGB1 stimulation resulted in significantly greater production of IL-6 and TNF-α by $CD24^{-/-}$ or $Siglecg^{-/-}$ DC than by WT DC (FIG. 4 Panel A). In contrast, CD24 or Siglec-G-deficiency did not affect the production of inflammatory cytokines by DCs in response to LPS or poly I:C (FIG. 4A).

Siglec-10 associates with the tyrosine phosphatase SHP-1, a known negative regulator of NF-κB activation. In a sub-population of B cells that reside in the peritoneum, the absence of Siglec-G results in the constitutive activation of NF-κB. To test whether activation of NF-κB by HMGB1 or LPS is affected by the absence of CD24 or Siglec-G, the nuclear translocation of the NF-κB subunit p65 in WT, $CD24^{-/-}$ and $Siglecg^{-/-}$ DCs were assayed. Both LPS and to a much lesser extent, HMGB1, induced nuclear translocation of p65 in WT DCs; however, in CD24 or Siglecg-deficient DCs, HMGB1 caused even greater increases in nuclear translocation of p65 than did LPS (FIG. 4 Panel B). These data suggest that the CD24-Siglec-G pathway may serve to decrease the host response to DAMPs, such as HMGB1, but not to TLR ligands of microbial origin (PAMPs), by selective repression of NF-κB.

To substantiate this hypothesis, a lethal dose of LPS was administered to WT, CD24$^{-/-}$ or Siglecg$^{-/-}$ mice. Neither the absence of Siglec-G nor CD24 affected the kinetics of LPS-induced lethality (FIG. 4 Panel C) or production of inflammatory cytokines (FIG. 4 Panel D). Despite an established contribution of HMGB1 to the late stage of sepsis, potential amplification of HMGB1 signaling by mutation of CD24 or Siglecg did not affect host survival in response to LPS. Therefore, CD24 and Siglec-G are selective modulators of the host response to HMGB1, but not to TLR ligands such as LPS, despite their potential to induce release of HMGB1.

In addition to nuclear DAMPs, such as HMGB1, DCs also respond to cytoplasmic DAMPs such as HSP70 and 90 by TLR-dependent mechanisms. To determine if the CD24-Siglec-G pathway also regulates host responses to HSP70 and 90, we first evaluated whether HSP70 and 90 associate with CD24 and Siglec-G. Reciprocal coimmunoprecipitations revealed that CD24 associates with both HSP70 and HSP90 (FIG. 4 Panel E). Similar to HMGB1, Siglec-G association with HSP70 and HSP90 was CD24-dependent (FIG. 4 Panel F) and CD24$^{-/-}$ and Siglecg$^{-/-}$ DCs produced significantly higher IL-6 and TNF-α in response to recombinant HSP70 and HSP90 (FIG. 4 Panel G) compared to WT DCs. These data reveal a critical role for CD24 and Siglec-G in negative regulation of DC response to multiple DAMPs.

Figure 5:
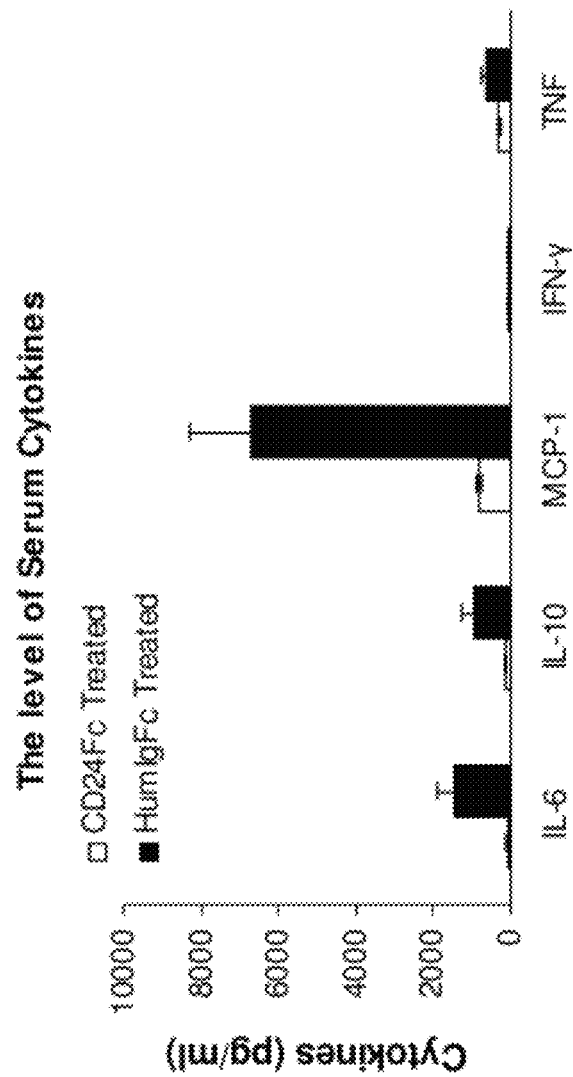

To test whether CD24Fc, a fusion protein that binds to HMGB1 and Siglec 10 can inhibit inflammatory response to AAP-induced liver damage, AAP was injected into WT B6 mice that also received CD24Fc or control Ig. WT mice received injection of AAP (16 mg/mouse, dissolved in H$_2$0) in conjunction with either CD24Fc or control IgG Fc. Serum was collected 5 hours after AAP injection and cytokines and ALT were measured by multiple cytokine beads array. Data shown are serum levels of the cytokines IL-6, IL-10, MCP-1, IFN-γ and TNF-α at 5 hours after AAP injection (mean±SE, n=5; *P<0.05 and **P<0.01, student t-test). As shown in FIG. 5, CD24Fc treatment resulted in massive reduction of inflammatory cytokines. These data demonstrated the potential of CD24Fc as a therapeutic reagent for tissue-injury induced inflammation.

Our results indicate that CD24 partners with Siglec-10 in humans or Siglec-G in mice to negatively regulate the immune response to proteins released by damaged cells, but not to ligands of microbial origin. Pattern recognition receptors such as TLRs and RAGE mediate activation induced by DAMP. Our data indicate that repression of response to HMGB1 may be achieved by inhibition of NF-κB activation. Inhibition may be mediated by SHP-1. SHP-1 associates with Siglec-10 via its ITIM motif and deficiency of either Siglec-G or SHP-1 enhances NF-κB activation. Given the role of HMGB1 in the pathogenesis of a number of diseases, including drug toxicity and liver and cardiac ischemia and reperfusion, this pathway may uncover new targets for disease intervention.

Although it is well established that the host can recognize "danger" induced by damaged tissue, information as to whether or how immune responses are triggered by tissue damage is limited is unknown. By identifying the CD24-Siglec-G pathway that selectively suppresses the immune response to DAMPs, the data presented herein provides a mechanism by which tissue injury and infection are distinguished, even though they both use the evolutionarily conserved TLR.

The following materials and methods were employed in the experiments.

Reagents. Recombinant proteins consisting of human IgG Fc and extracellular domains of SIglec 5, 7, 10 and 11 were purchased from R&D Systems. Horseradish peroxidase conjugated anti-mouse, or anti-rabbit secondary-step reagents, as well as anti-p65 and anti-sp1 were purchased from Santa Cruz Biotechnology. Anti-FLAG M2 affinity gel, anti-FLAG mAb, acetaminophen (AAP) and lipopolysaccharide (LPS, from E. coli 055:B5) were purchased from Sigma (St Louis, Mo.). The composition CD24Fc have been described, the product is obtained from Oncolmmune, Inc. (Columbus, Ohio). Human HSP70, HSP90 and anti-mouse Hsp70, Hsp90 antibodies were purchased from Biovision, Inc. (Mountain View, Calif.). The anti-HMGB-1 antibodies 3E8 and 3B1 are described below.

Figure 6:
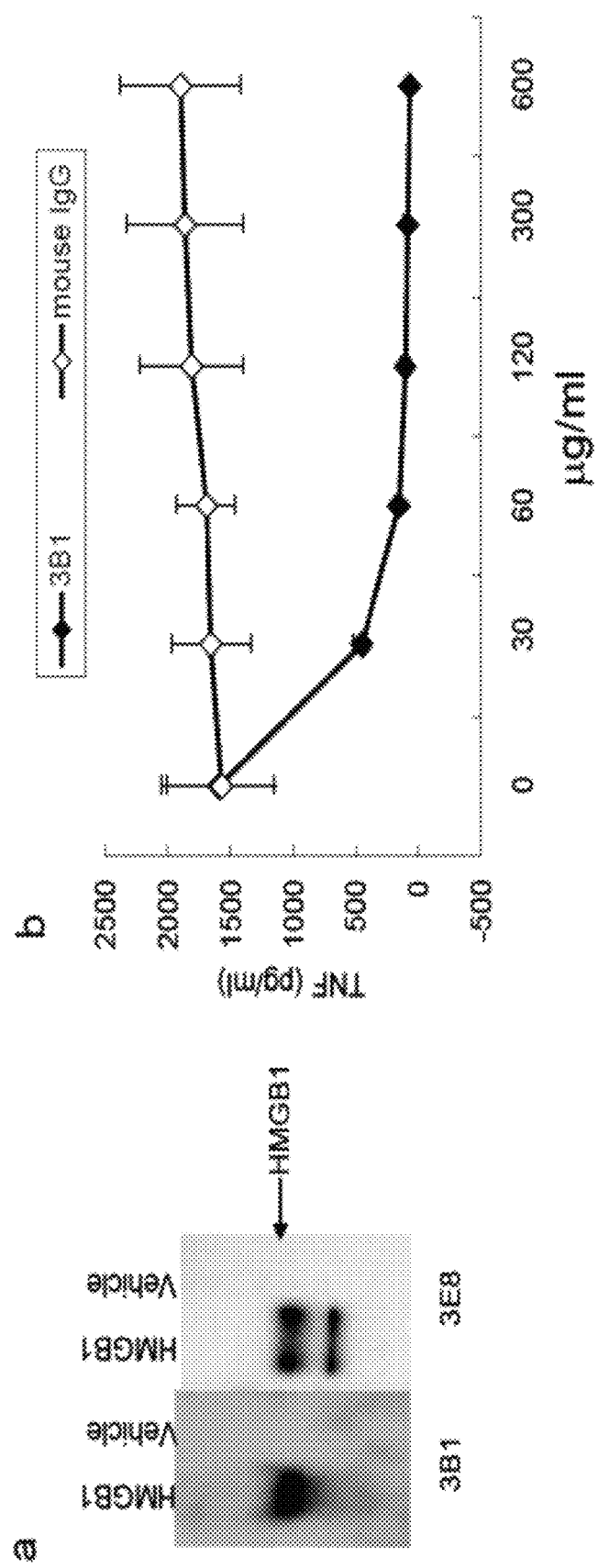

Characterization of HMGB-1 antibodies used for the study. HMGB-1 is highly conserved (98% identity between mouse and human). In order to break immune tolerance, we introduced a universal T cell epitope from a *mycobacterium tuberculosis* Ag 5 into C-terminus of HMGB-1 and the resulting recombinant protein was used as an antigen for immunization. With the help of the T cell epitope and autoimmune NZB/W mice, we were able to obtain a panel of mouse anti-HMGB-1 antibodies that cross-react with mouse and human HMGB-1. Two of them, 3E8 and 3B1 were used in this study. As shown in FIG. 6A, both antibodies react with recombinant HMGB-1 in Western blot. In pilot studies, we have found 3E8 to be a more efficient in immunoprecipitation and Western blot than 3B1 (data not shown). Moreover, 3B1 completely blocked production of TNFα by DC after stimulation of recombinant HMGB-1 (FIG. 6Bb).

cDNAs encoding either full-length or specifically truncated human HMGB1 and N-FLAG-tagged wild-type (WT) or mutant (119R>A) Siglec10 were cloned into expression vector pCMV-Tag 2B (Sigma). All constructs were verified by DNA sequencing. For purification of FLAG-tagged HMGB-1, the full-length HMGB-1 expression vector was transfected into TSA cells, the lysates were used as source to purify recombinant HMGB-1 according to a reported procedure.

Experimental animals: Mice with targeted mutations of CD24 and Siglecg were produced from ES cells of C57BL/6 origin as described. Age- and sex-matched wild type C57BL/6 mice were used as controls. All mice were used at 6-8 weeks of age. All procedures involving mice have been approved by the University Animal Use Regulatory Committees.

Mouse pathological findings: For ALT measurements, blood was collected at given time points. Serum was isolated by centrifugation of clotted blood at 12,000×g for 10 min at room temperature and then sent to Animal Diagnostic Laboratory of Animal Research Facility, University of Michigan (Ann Arbor, USA) for determining ALT activity. For histology, the mouse livers were removed and immediately fixed in 4% formaldehyde-PBS solution, embedded in paraffin, sectioned at 5 μm, and stained with hematoxylin and eosin. Serum cytokines were determined using mouse cytokine bead array designed for inflammatory cytokines (Cat. No 552364, BD Biosciences).

Flow cytometric analysis for Siglec10 ligands: Spleen cells from WT or CD24$^{-/-}$ mice were washed in buffer A (150 mM NaCl, 3 mM MnCl$_2$, 1 mM CaCl$_2$, 1 mM MgCl$_2$, 25 mM Tris, pH 7.6, 2% BSA), and incubated for 1 hour at 37° C. with 1 μg of Siglec-10-Fc or Fc control. The bound receptors were detected with PE conjugated anti-human IgG-Fc and analyzed on a BD LSII.

Immunoprecipitation and immunoblotting: Cell lysates were prepared in the buffer B (1% Triton X-100, 150 mM NaCl, 3 mM MnCl$_2$, 1 mM CaCl$_2$, 1 mM MgCl$_2$, 25 mM Tris, pH 7.6) and protease inhibitors (1 μg/ml leupeptin, 1 μg/ml aprotinin and 1 mM phenylmethylsulfonyl fluoride). Samples were pre-cleared with 60 µl of protein A-conjugated agarose beads (Upstate, Lake Placid, N.Y.) for 2 h at 4° C. or 37° C. with rotation, and then incubated with corresponding antibodies (anti-CD24 mAbs M1/69 and 20C9, 10 µg/ml; anti-HMGB-1, 2 µg/ml; anti-HSP70 and HSP90 antibodies, 3 µg/ml). The beads were washed four times with buffer B and re-suspended in SDS sample buffer for Western blot analyses with given antibodies (0.5 µg/ml). The anti-Siglec-G antisera were used at 1:100 dilution.

Confirmation of CD24-HMGB-1 interaction by mass-spectrometry. The lysates from WT and CD24-deficient hosts were incubated with anti-CD24 mAbs (a mixture of 20C9 and M1/69 and precipitated with protein G beads. The precipitates were incubated with the EDTA to release cation-dependent binding. The eluted proteins were subject to trysinization followed by mass-spectrometry analysis. The data shown in Table 1 are peptides identified from WT spleen cells, and no HMGB-1 peptides were identified from the immunoprecipitates of the CD24–/– spleen cells.

Mass spectrometry: After gel concentration, the protein samples were submitted to Taplin Spectrometry Facility at Harvard Medical School for high throughput analysis.

TABLE 1

HMGB-1 Peptide Fragments Ascertained by Mass Spectrometry Peptide Matches

| Position | Sequence | SEQ ID NO. |
|---|---|---|
| 57-64 | GKFEDMAK | 1 |
| 154-162 | YEKDIAAYR | 2 |
| 76-85 | TYIPPKGETK | 3 |
| 30-42 | HPDASVNFSEFSK | 4 |
| 114-126 | GEHPGLSIGDVAK | 5 |
| 29-42 | KHPDASVNFSEFSK | 6 |
| 112-126 | IKGEHPGLSIGDVAK | 7 |
| 128-145 | LGEMWNNTAADDKQPYEK | 8 |
| 127-145 | KLGEMWNNTAADDKQPYEK | 9 |

Statistical Analysis: The differences in cytokine proteins and ALT activities were analyzed by Student's t test. The differences in survival rates were analyzed by Kaplan-Meier survival analysis with log-rank test.

The present investigators have also identified that disruption of sialic acid-based pattern recognition exacerbates polybacterial sepsis.

Inflammation is a critical determinant of pathogen virulence in some of the most challenging infectious diseases. Pathogen-associated and/or danger-associated molecular patterns (PAMP and DAMP, respectively) are two well-known inducers of inflammation. Because CD24-Siglec G/10 interaction selectively represses inflammatory response to DAMP, microbial disruption of the negative regulation would provide a general mechanism to exacerbate inflammation. Here we show that the sialic acid-based pattern recognition of CD24 by Siglec G/10 is targeted by sialidases in polybacterial sepsis. Sialidase inhibitors protect mice against sepsis by a Siglecg-dependent mechanism, whereas a targeted mutation of either CD24 or Siglecg exacerbates sepsis. Our results demonstrate a role for disrupting sialic acid-based pattern recognition in microbial virulence and indicate a therapeutic approach to dampen the harmful inflammatory response during infection.

While DAMPs released during infection trigger inflammation through TLR and/or NLR receptors, our studies have indicated that host response to DAMP is negatively regulated by CD24-Siglec G/10 interactions. As a result, inflammation to DAMPs is limited unless the CD24-Siglec G (mouse)/10 (human) interaction is disrupted. Therefore, we determined whether the CD24-Siglec G/10 interaction may be targeted by pathogens during infection.

Figure 14:
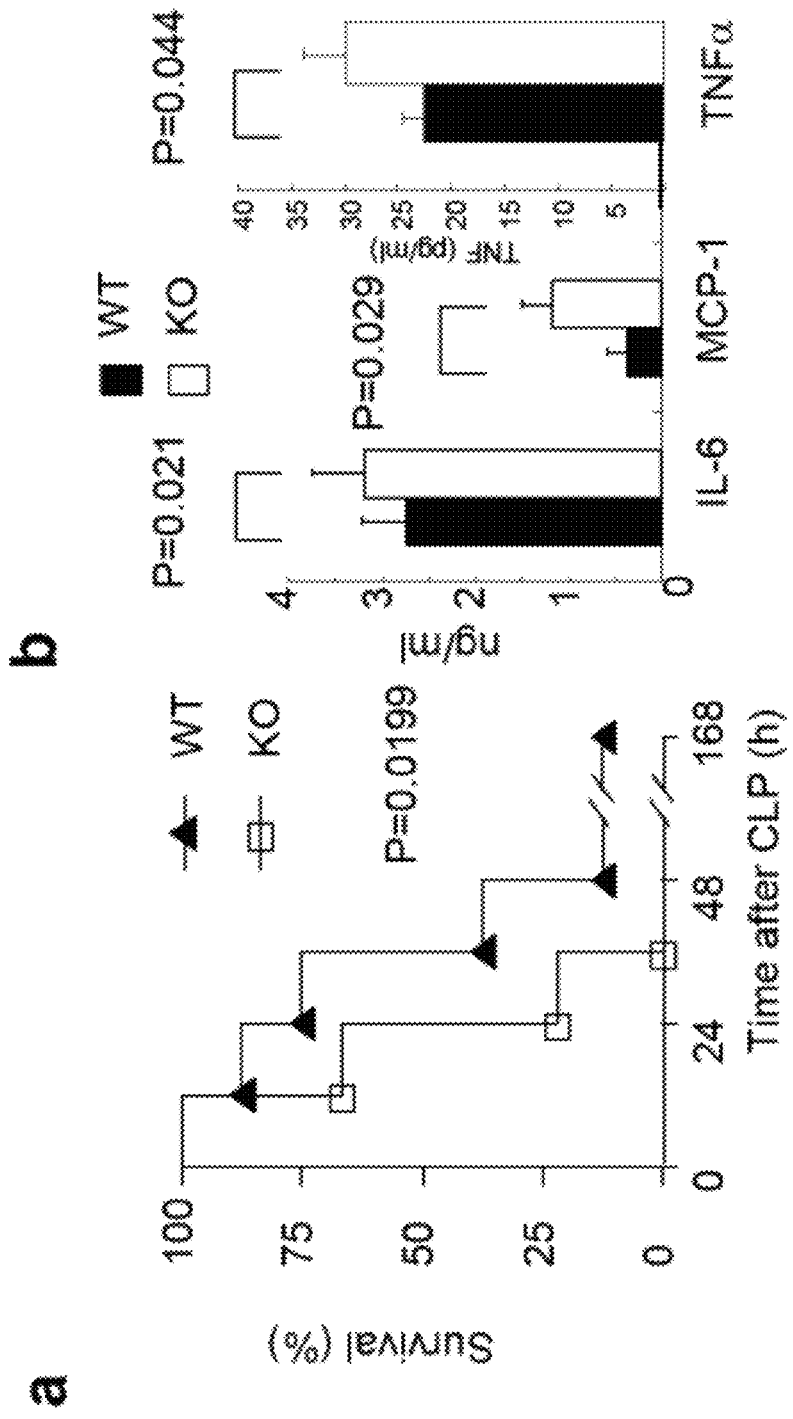

Siglec G/10 is a member of Siglecs, immunoglobulin super family lectins with a defining feature of recognizing sialic acid-containing structures. We used cecal ligation and puncture (CLP) as a basic model to evaluate the potential contribution of CD24-Siglec G interaction in lethal sepsis. As shown in FIGS. 10(a) and 10(b), targeted mutations resulted in significant acceleration of onset and increased mortality following CLP, even though the bacterial burden in the blood was unaffected by these mutations. The increased severity corresponds to a massive increase of inflammatory cytokine (FIG. 10(c)). Since CD24 is broadly expressed, we tested the contribution of CD24 on hematopoietic cells using irradiation chimera consisting of either WT or CD24–/– hematopoietic cells in the irradiated CD24–/– host. As shown in supplemental FIG. 14, CD24-expression in the hematopoietic cells significantly prolonged life of the CLP mice and repressed production of inflammatory cytokines. Since our prior experiments demonstrated that CD24–/– dendritic cells (DC) produced higher levels of inflammatory cytokines in response to DAMP, we produced transgenic mice with DC-exclusive CD24 expression (FIG. 10(d)) to determine whether CD24 expression on DC alone is sufficient to convey protection. Because transgenic mice produced significantly less inflammatory cytokines and showed better survival than the CD24-deficient littermates (FIG. 10(e), (f)), CD24 mediates protection at least partially by suppressing inflammatory cytokine production by DC.

Figure 11:
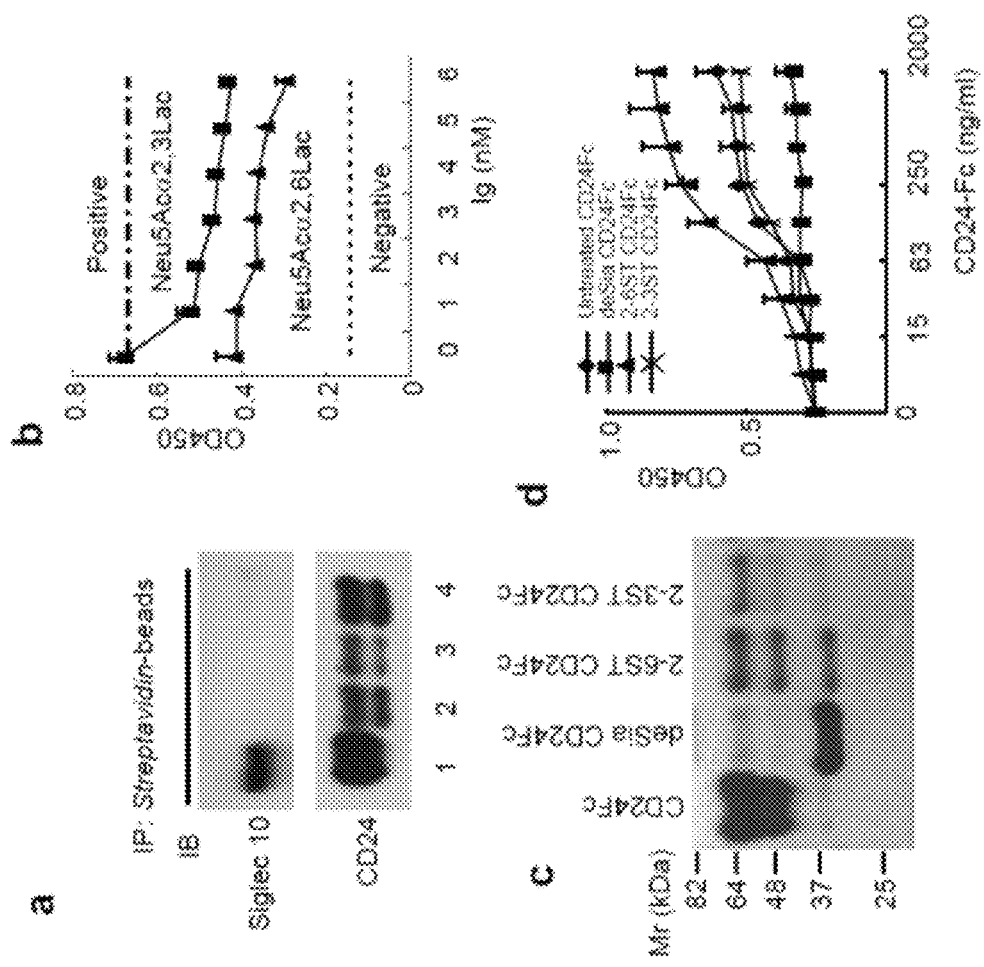
Figure 15:
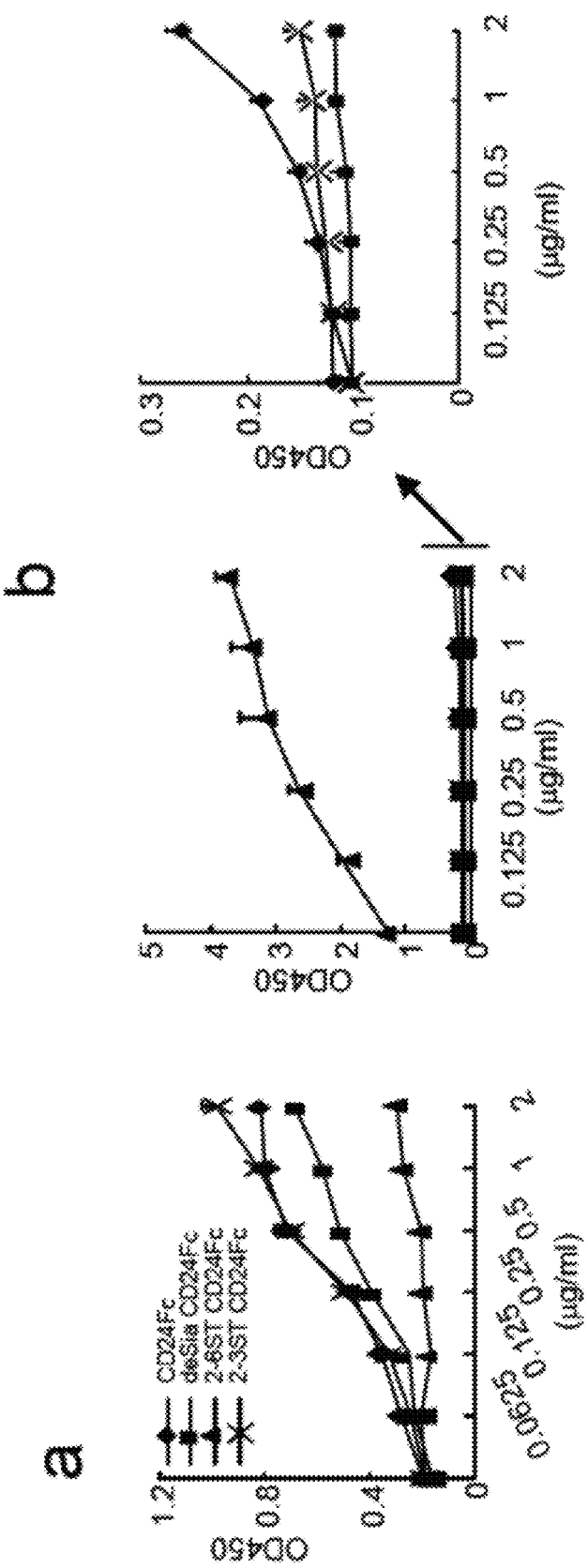

The impact of genetic disruption of the CD24-Siglec G interaction indicates that this pathway negatively regulates inflammation during sepsis and thus raises an intriguing possibility this interaction may be targeted to exacerbate sepsis. Because many pathogenic bacteria encodes sialidases as their virulence factor, and because sialic acid-based pattern recognition is a cardinal feature of Siglec, we considered the possibility that bacterial sialidase may exacerbate sepsis by CD24 desialyation. To determine whether the CD24-Siglec 10 interaction may be susceptible to bacterial sialidase, we treated the CD24Fc with recombinant sialidases of three different bacteria known to cause sepsis, including *Streptococcus pneumoniae, Clostridium perfringens*, and *Vibrio cholerae*. The interaction between CD24 and Siglec 10 fusion proteins were measured by co-immunoprecipitation and a solid-phase binding assay. Regardless of their specificities for either 2-3-, or 2-3- and 2-6-, or 2-3-, 2-6- and 2-8-linked sialic acids, all sialidases abolished CD24-Siglec 10 interaction. The interaction was inhibited by either 2-3 or 2-6-linked sialoside, although the 2-6 sialoside was more potent (FIG. 11(b)). In combination, the data of enzyme digestion and inhibition by sialoside suggest that both types of sialosides could interact with Siglec 10. We used sialidase-desialylated with and without additional sialyltransferase-resialylated CD24Fc (FIG. 15) to substantiate these observations. As shown in FIGS. 11(c) and (d), either 2-3 or 2-6 resialylation was sufficient to restore CD24-Siglec 10 interaction. Nevertheless, untreated CD24 may require both forms of sialosides to achieve optimal binding to Siglec 10, since sialyation was likely heterogeneous and less efficient under physiological conditions.

Figure 12E:
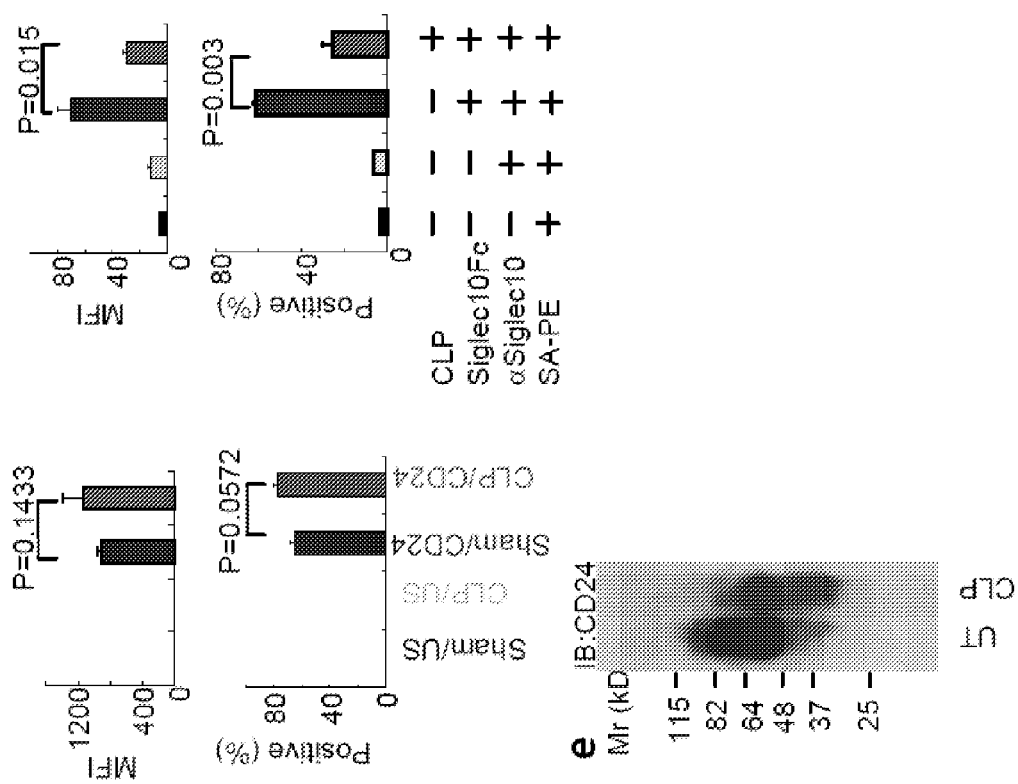

We then tested the potential role for sialidase in the CLP model. As shown in FIG. 12(a), following CLP, a clear elevation of serum sialidase activity was observed. Because no increase in circulating sialidase activity was detected in LPS-treated mice, the elevated sialidase activity is likely of bacterial origin. Sera from CLP mice, but not those from sham-surgery control, disrupted CD24-Siglec 10 interaction (FIG. 12(b)). In order to determine whether CD24 was modified during CLP, we analyzed both total levels and the molecular weight distribution of CD24, which is heterogeneous due to extensive glycosylation. Although the total level of CD24 was not altered in the CLP group, a substantial reduction of Siglec 10-binding was observed by flow cytometry (FIG. 12(c), (d)). Corresponding to reduced Siglec 10-binding activity, increased electrophoresis mobility was observed in CD24 on the spleen cells from the CLP mice (FIG. 12(e)).

Figure 13:
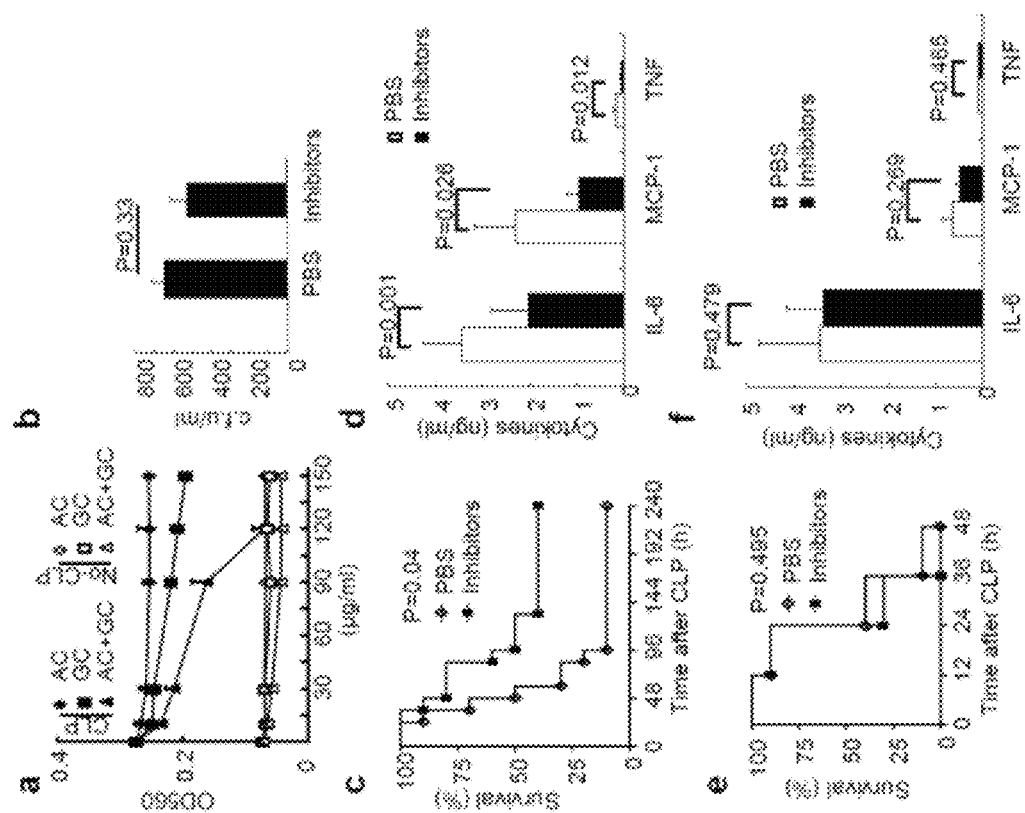

To test the role of bacterial sialidases in pathogenesis of sepsis, we synthesized two sialidase inhibitors, 2,3-dehydro-2-deoxy-N-acetylneuraminic acid (Neu5Ac2en) and 2,3-dehydro-2-deoxy-N-glycolylneuraminic acid (NeuGc2en). We first tested their inhibition of sialidase activity in the serum of sepsis mice. As shown in FIG. 13(a), while Neu5Ac2en had minimal effect on the sialidase activity, a partial inhibition was observed for Neu5Gc2en. A combination of the two inhibitors completely inhibited the sialidase activity in the sera of sepsis mice. Although the inhibitors did not reduce bacterial burden in the blood (FIG. 13(b)), they significantly reduced the mortality of sepsis (FIG. 13(c)). Correspondingly, multiple inflammatory cytokines were reduced by the inhibitors (FIG. 13(d)). To confirm that the sialidase inhibitors protect mice by preserving the integrity of CD24-Siglec G interaction, we tested their activity in mice with targeted mutation of Siglecg. As shown in FIGS. 13(e) and (f), no protection was observed in the Siglecg-deficient mice. The dependence on the Siglecg gene demonstrates a specificity of the inhibitors and suggests that the protection is achieved by preserving the Siglec G-CD24 interaction.

Taken together, we have shown that CD24-Siglec 10/G interaction is a key regulator for polybacterial sepsis. Since a combination of two sialidase inhibitors conveyed a significant therapeutic effect, sialidases may represent valuable therapeutic targets for sepsis. It is of note that many pathogens, including viruses and bacteria encode their own sialidases, which are also known as neuraminidase. In both viruses and bacteria, the sialidases have been shown as virulence factors, although a sialidase from *Streptococcus pneumoniae* may protect mice against intravascular coagulation during sepsis. Until now, virulence and the sialidase function were largely viewed from the prism of pathogen growth. Our results presented herein have demonstrated that sialidase can regulate virulence by a bacterial growth-independent mechanism; i.e., by disruption of pattern recognition that selectively represses host response to tissue injuries. Since tissue injury is common during infections, it is likely that the sialidases from other pathogens also affect virulence by targeting the CD24-Siglec 10 interaction.

The current paradigm for the cause of inflammation emphasizes interaction between PAMP, DAMP and their receptors. Our results demonstrate that in addition to providing PAMP and DAMP, microbes can exacerbate innate immunity by disrupting sialic acid-based pattern recognition. This would further strengthen the discrimination between septic and aseptic insults. Therefore, an effective strategy to control excessive inflammation can target both production of and regulation of the host response to DAMP and PAMP.

The following procedures were used in the experiments.

Figure 16:
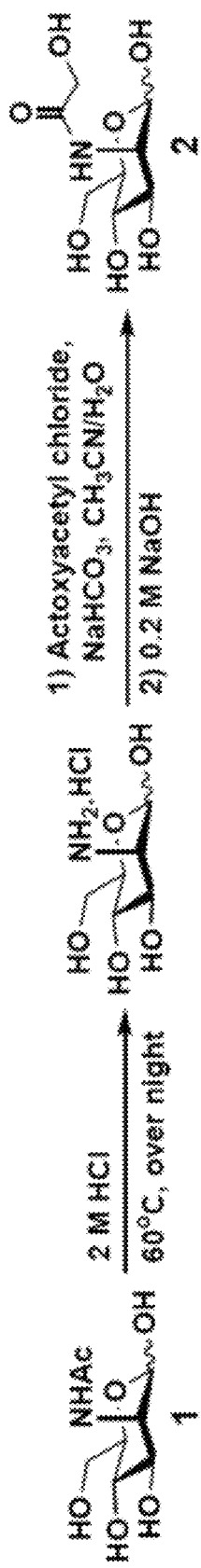
FIG. 16 depicts the synthesis of N-glycolylmannosamine (ManNGc) from ManNAc.
Figure 17:
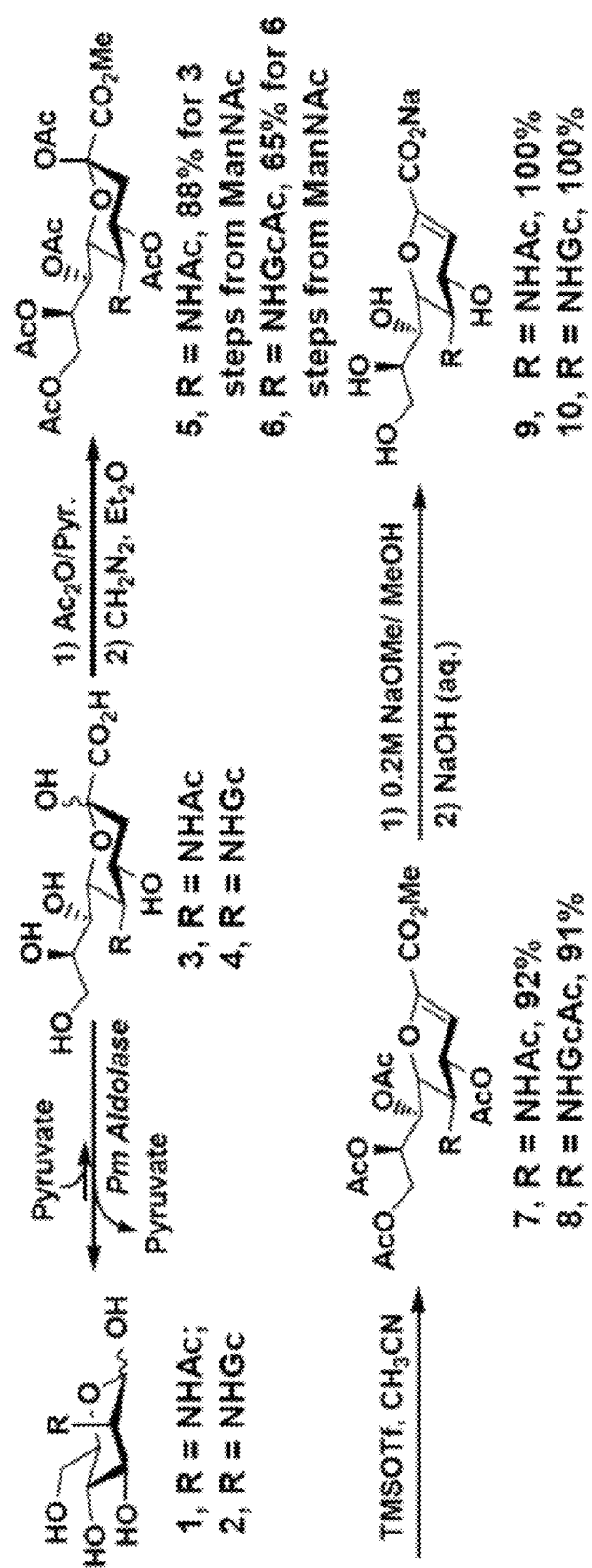
FIG. 17 depicts the chemoenzymatic synthesis of Neu5Ac2en.

Reagents included the following materials. Recombinant protein consisting of human IgG Fc and extracellular domains of Siglec 10 and biotinylated anti-human Siglec 10 antibody were purchased from R&D Systems. Horseradish perioxidase conjugated anti-mouse IgG was purchased from Santa Cruz Biotechnology. Lipopolysaccharide (LPS, from *E. coli* 055:B5), α2-3 sialidase (N7271, from *Streptococcus pneumoniae*), and α2-3/6 sialidase (N5521, from *Clostridium perfringens*) were purchased from Sigma (St Louis, Mo.). Sialidase (11082340, from *Vibrio cholerae*) was purchased from Roche. Pierce Avidin Agarose beads were purchased from Thermo Scientific (Rockford, Ill.). Anti-mouse CD24-PE, anti-mouse CD11c-APC, and PE-streptavidin were purchased from eBioscience. Anti-human CD24 (Cat: 555426) was purchased from BD Pharmingen™. Amplex® Red Neuraminidase Assay Kit (A22178) was purchased from Molecular Probes. Neu5Acα2-3Lac and Neu5Acα2-6Lac were synthesized as described in Deng, R., Herceg, E. & Trenary, M. Identification and hydrogenation of C2 on Pt(111). *Journal of the American Chemical Society* 127, 17628-17633 (2005) and Yu, H. et al. Highly efficient chemoenzymatic synthesis of naturally occurring and non-natural alpha-2,6-linked sialosides: a *P. damsela* alpha-2,6-sialyltransferase with extremely flexible donor-substrate specificity. *Angewandte Chemie International ed* 45, 3938-3944 (2006). Neu5Ac2en and Neu5Gc2en were synthesized as described in FIG. 16 and FIG. 17.

Experimental animals CD24−/− and Siglecg−/− C57BL/6 mice are described by Ding, C. et al. Siglecg limits the size of B1a B cell lineage by down-regulating NFkappaB activation. *PloS one* 2, e997 (2007) and Nilsson, N., Wallen-Ohman, M., Ohlin, M. & Borrebaeck, C. A. Altered gene expression associated with apoptosis in a pre-B-leukemic cell line following cross-linking of MHC class I. *Exp Cell Res* 231, 190-197 (1997). Transgenic mice expressing CD24 under the control of CD11c promoter, $CD24^{CD11ctg}$, were produced using a previously described CD11c transgenic construct; see Brocker, T., Riedinger, M. & Karjalainen, K. Driving gene expression specifically in dendritic cells. *Adv Exp Med Biol* 417, 55-57 (1997) and Chen, M. et al. Dendritic cell apoptosis in the maintenance of immune tolerance. Science 311, 1160-1164 (2006). Mice with DC-exclusive CD24 expression were produced by crossing the $CD24^{CD11ctg}$ transgene into the CD24−/− background. Irradiation bone-marrow chimera were produced using $5 \times 10^6$ bone marrow cells from either WT or CD24−/− mice as donors and the lethally (1,200 Rad) irradiated CD24−/− recipients, as described in Chen, C. et al. TSC-mTOR maintains quiescence and function of hematopoietic stem cells by repressing mitochondrial biogenesis and reactive oxygen species. *The Journal of experimental medicine* 205, 2397-2408 (2008). All procedures involving mice have been approved by the University of Michigan Animal Care and Use Committee.

Cecal Ligation and Puncture. The procedure for lethal CLP was performed as described in Rittirsch, D., Huber-Lang, M. S., Flierl, M. A. & Ward, P. A. Immunodesign of experimental sepsis by cecal ligation and puncture. *Nature protocols* 4, 31-36 (2009). Briefly, mice were anesthetized with isoflurane anesthesia. Through a midline incision, the cecum was exteriorized and tightly ligated 1 cm from its base with 3-O silk. The cecum was then punctured through-and-through once with a 21 gauge needle. A small amount of stool was expelled from the puncture before the cecum was replaced into the peritoneal cavity and the abdominal incision closed. An amount of 100 µl sterile saline or sugar was administered by i.p. injection immediately after CLP. The CLP were performed blinded to the identities of the treatment groups and/or genotypes of the mice. Mortality was assessed twice a day for at least 7 days.

Flow cytometric analysis for Siglec10 ligands. Spleen cells from normal WT or CLP treated WT mice were washed in buffer A (150 mM NaCl, 3 mM $MnCl_2$, 1 mM $CaCl_2$, 1 mM $MgCl_2$, 2% BSA Tris-HCl, pH 7.6), and incubated for 1 hour on ice with 1 µg of Siglec10 Fc. The cells were washed and then incubated with biotinylated-anti-Siglec 10 antibody (0.05 µg/ml) for another hour on ice. The bound receptor was detected with PE conjugated streptavidin and analyzed on a BD LSII.

Measurement of inflammatory cytokines. Blood was obtained at indicated time points. Cytokines in the serum were determined using mouse cytokine bead array designed for inflammatory cytokines (552364, BD Biosciences).

Microplate binding assay. Ninety-six well plates were coated with either untreated, desialyated or resialyated CD24 in 50 mM carbonate/bicarbonate buffer, pH 9.5, overnight at 4° C. Wells were blocked with binding buffer (20 mM HEPES, 2% bovine serum albumin, 150 mM NaCl, 3 mM $MnCl_2$, 1 mM $CaCl_2$, 1 mM $MgCl_2$, pH 7.6) for 1 hour. Siglec 10 Fc (1 µg/ml) was added to the plate and incubated for 2 hours. Between incubations (all at 37° C.), the plates were washed five times with the binding buffer. Biotinylated-anti-Siglec 10 antibody (0.05 µg/ml) was used to detect bound Siglec 10Fc. The plate-associated biotinylated proteins were detected by horseradish peroxidase (HRP)-conjugated streptavidin (1:1,000) for 1 hour and development with 100 µl/well p-nitrophenyl phosphate liquid substrate system. Absorbance at 450 nm was recorded.

Immunoprecipitation and immunoblotting. Biotin conjugated human CD24Fc was digested with various kinds of sialidase for 16 hours at 37° C. and then incubated with 1 µg/ml Siglec 10 Fc in buffer A. Siglec 10 bound to the CD24 was immunoprecipitated with streptavidin-beads. Immunoprecipitates were washed 4 times with buffer A and resuspended in SDS sample buffer for Western blot analysis.

Sialidase-desialylation and sialyltransferase-resialyation of CD24 were carried out as described below.

Serum neuraminidase assay. The neuraminidase activity in serum was measured according to the procedure provided in Amplex® Red Neuraminidase Assay Kit (Cat. No. A22178).

Statistical analysis. The differences in cytokine proteins were analyzed by Student's t test. The differences in survival rates were analyzed by Kaplan-Meier plot and the statistical significance was determined using a log-rank test.

Expression of enzymes. A recombinant sialidase cloned from *Bifidobacterium infantis* (S2), a CMP-sialic acid synthetase cloned from *Neisseria meningitidis* (NmCSS), an α2-3-sialyltransferase cloned from *Pasteurella multocida* (PmST2), and an α2-6-sialyltransferase cloned from *Photobacterium damsela* were used for CD24 glycan redecoration. All of these recombinant enzymes have an N-terminal or a C-terminal $His_6$-tag to facilitate their immobilization to Ni-NTA resins and separation from CD24 after the desialylation or sialylation reactions.

*E. coli* BL21 (DE3) cells carrying the recombinant plasmid were cultured in LB-rich medium supplemented with ampicillin (100 mg/ml). Overexpression of the target protein was achieved by inducing the *E. coli* cell culture with IPTG (0.3 mM for sialidase and 0.1 mM for other enzymes) when the $OD_{600\,nm}$ of the culture reached 0.6 followed by incubating at 20° C. for 24 hours with vigorous shaking at 250 rpm in a C25KC incubator shaker (New Brunswick Scientific, Edison, N.J.).

Immobilization of enzymes to Ni-NTA beads. To obtain the cell lysate, cell pellet harvested by centrifugation at 4000 rpm for 2 hours was resuspended in a lysis buffer (pH 8.0, 100 mM Tris-HCl containing 0.1% Triton X-100) (20 mL/L cell culture). Lysozyme (50 mg/ml) and DNase I (3 mg/ml) were then added and the mixture was incubated at 37° C. for 60 minutes with vigorous shaking. Cell lysate was obtained by centrifugation at 12,000 rpm for 30 minutes as the supernatant. To immobilize the enzyme, lysate (5 ml) was mixed with pre-washed Ni-NTA agarose resin (1 ml) and incubated for 30 min. The beads were then separated from the lysate by centrifugation and washed with 3 rounds of 1× washing buffer (50 mM Tris-HCl, pH 8.0, 500 mM NaCl, 20 mM imidazole) and 1 round of 1× reaction buffer (50 mM MES buffer, pH 5.0).

Sialidase treatment of CD24. Recombinant CD24 (30 mg) was incubated with sialidase immobilized on beads (1 ml) in a total volume of 5 ml in 1× reaction buffer (50 mM MES buffer, pH 5.0) for 4 h at 37° C. with gentle shaking. The beads were simply removed by centrifugation at 4000 rpm for 5 min. The solution containing sialidase treated CD24 was subjected to extensive dialysis against dialysis buffer containing activated charcoal to remove the Neu5Ac released from the CD24 by the sialidase. The dialysis buffer was changed every 24 hours until no Neu5Ac was detected in the desialylated CD24 by 1,2-diamino-4,5-methylenedioxybenzene (DMB)-conjugation derivatization followed by HPLC fluorescent analysis.

α2-3 or α2-6-sialylation of desialylated CD24. Desialylated CD24 (10 mg) was re-sialylated to form exclusively α2-3- or α2-6-sialyl linkage using 50 equivalents of Neu5Ac and CTP in a one-pot two-enzyme system containing a recombinant *Neisseria meningitidis* CMP-sialic acid synthetase (NmCSS) and a *Pasteurella multocida* α2-3-sialyltransferase (PmST2) (for the formation of α2-3-sialyl linkage) or a *Photobacterium* damsela α2-6-sialyltransferase (for the formation of α2-6-sialyl linkage). Reactions were carried out in a total volume of 4 ml in 100 mM Tris-HCl (pH 8.0) buffer for 4 hours at 37° C. with gentle shaking. The beads were then simply removed by centrifugation at 4000 rpm for 5 min. Extensive dialysis against activated charcoal was performed to remove excess amount of Neu5Ac, CTP, and CMP byproducts.

Synthesis of sialidase inhibitors. The 2,3-dehydro-2-deoxy sialic acid derivatives, Neu5Ac2en (molecule "9" in FIG. 17) and Neu5Gc2en (molecule "10" in FIG. 17), were synthesized using a chemoenzymatic approach. For synthesizing Neu5Gc2en, N-glycolylmannosamine (ManNGc) ("2") was prepared from ManNAc in three steps (FIG. 16) by deactylation of the N-acetyl group, coupling the resulted free amine with acetoxyacetyl chloride, and deacetylation of the O-acetyl group. Crude ManNGc was used in the enzymatic synthesis of Neu5Gc without any purification.

Chemoenzymatic synthesis of Neu5Ac2en ("9" in FIG. 17) was carried out from commercially available N-acetylmannosamine (ManNAc) which was converted to Neu5Ac using a *Pasteurella multocida* sialic acid aldolase-catalyzed reaction. The Neu5Ac was then fully protected in two steps to produce peracetylated methyl ester in 88% yield for three steps from ManNAc. This ester went through trifluoromethanesulfonate (TMSOTf)-catalyzed elimination condition to produce 2,3-dehydro-2-deoxy product in 92% yield. Deprotection with NaOMe/MeOH followed by NaOH (0.2 M), neutralization with H+ resin, purification with silica gel chromatography, and desalting with BioGel P2 gel filtration column produced Neu5Ac2en in quantitative yield.

Chemoenzymatic synthesis of Neu5Gc2en ("10") was carried out similarly as described above for the synthesis of Neu5Ac2en ("9") except that ManNGc instead of ManNAc was used as a starting material for the aldolase-catalyzed reaction. The fully protected Neu5Gc methyl ester was purified in 65% yield for six steps from ManNAc, which was further converted to the final Neu5Gc2en.

Inhibitors for the sialidases from *S. pneumoniae* are now described as examples to illustrate methods to generate selective sialidase inhibitors and derivatives thereof. *S. pneumoniae* is the leading cause of secondary bacterial pneumonia and a common causative agent for sepsis. Therefore *S. pneumoniae* sialidases are used as the targets for inhibitors. Three distinct sialidases, NanA, NanB and NanC, are encoded in the *S. pneumoniae* genome. They are cloned using synthetic genes with codons optimized for an *E. coli* expression system, using DNA templates for polymerase chain reactions, to obtain sufficient quantities of proteins for drug screening.

The protein crystal structures of a truncated NanA (56.5 kDa) of *S. pneumoniae* (CNanA) containing the catalytic domain that retained full enzyme activity (13), *S. pneumoniae* NanB, human cytosolic sialidase NEU2, and several influenza virus neuraminidases in complex with inhibitor Neu5Ac2en or Zanamivir (a 4-deoxy-4-N-guanidino derivative of Neu5Ac2en) have been reported. Despite their primary sequence differences, bacterial, viral, and human sialidases share a common canonical six-bladed β-propeller fold. Comparing the conformation of the bound inhibitors (FIG. 18) and the protein inhibitor-binding pockets (FIG. 19A-D) of four sialidases reveals differences among four inhibitor-binding sites. The most significant difference between the bacterial sialidases (CNanA and NanB) and the human NEU2 is the interaction of Neu5Ac2en C9-OH with the proteins. The C9-OH of inhibitor Neu5Ac2en makes extensive contacts with NEU2 but only limited interaction with CNanA and NanB. In addition, C9-OH of Neu5Ac2en in CNanA points toward a relatively long tunnel, and the C9-OH of Neu5Ac2en in NanB is also close to a big cavity. These suggest that adding an alkyl ether (such as methyl, ethyl, propyl, or a butyl group) at the C9-OH of Neu5Ac2en may provide inhibitors with improved inhibitory activity and enhanced selectivity for bacterial sialidases CNanA and NanB compared to human NEU2.

Figure 18:
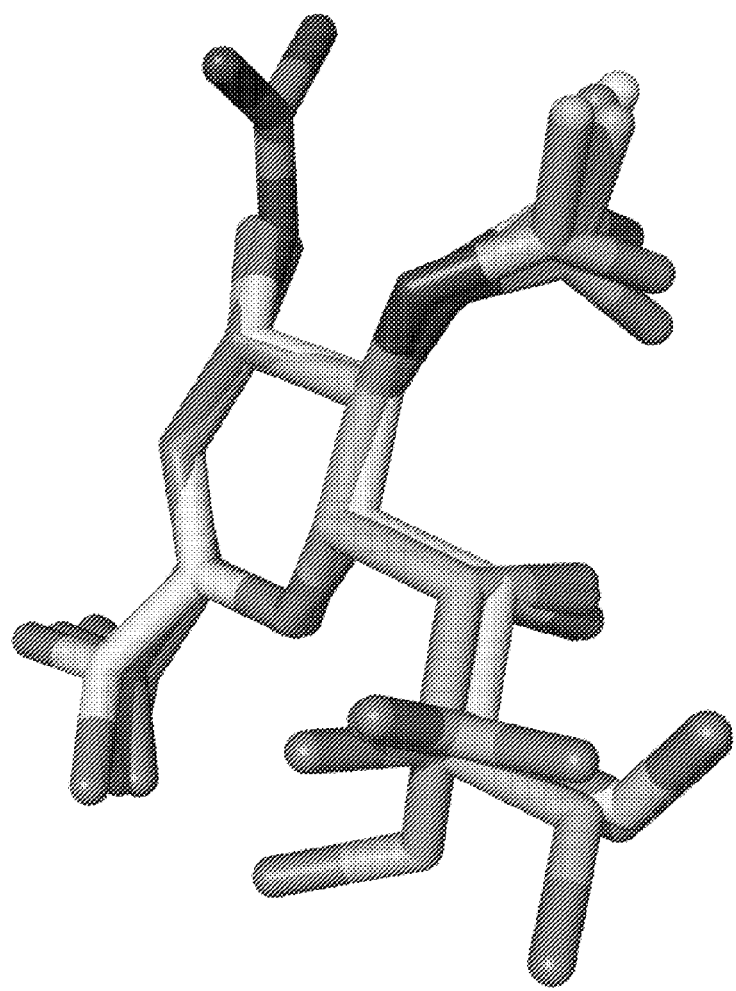
FIG. 18 shows an overlay of Zanamivir (carbons are shown in purple) bound to 18NA and Neu5Ac2en bound to CNanA (carbons are shown in green), NanB (carbons are shown in light blue), and NEU2 (carbons are shown in yellow).
Figure 19A:
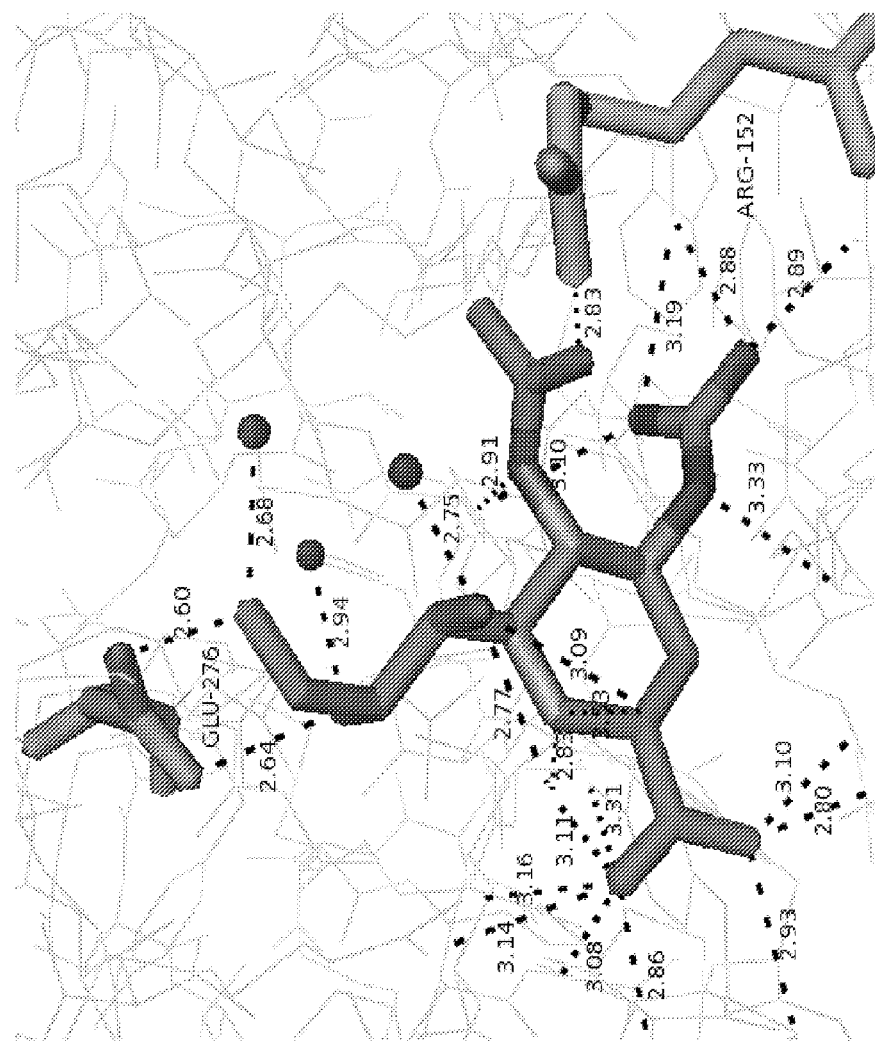
FIG. 19 shows the interaction of sialidases and inhibitors, where the panels show: (A) catalytic domain of *S. pneumoniae* NanA (CNanA) with Neu5Ac2en; (B) *S. pneumoniae* NanB with Neu5Ac2en; (C) human NEU2 with Neu5Ac2en; and (D) 1918 influenza virus H1N1 neuraminidase (18NA) with Zanamivir.
Figure 19B:
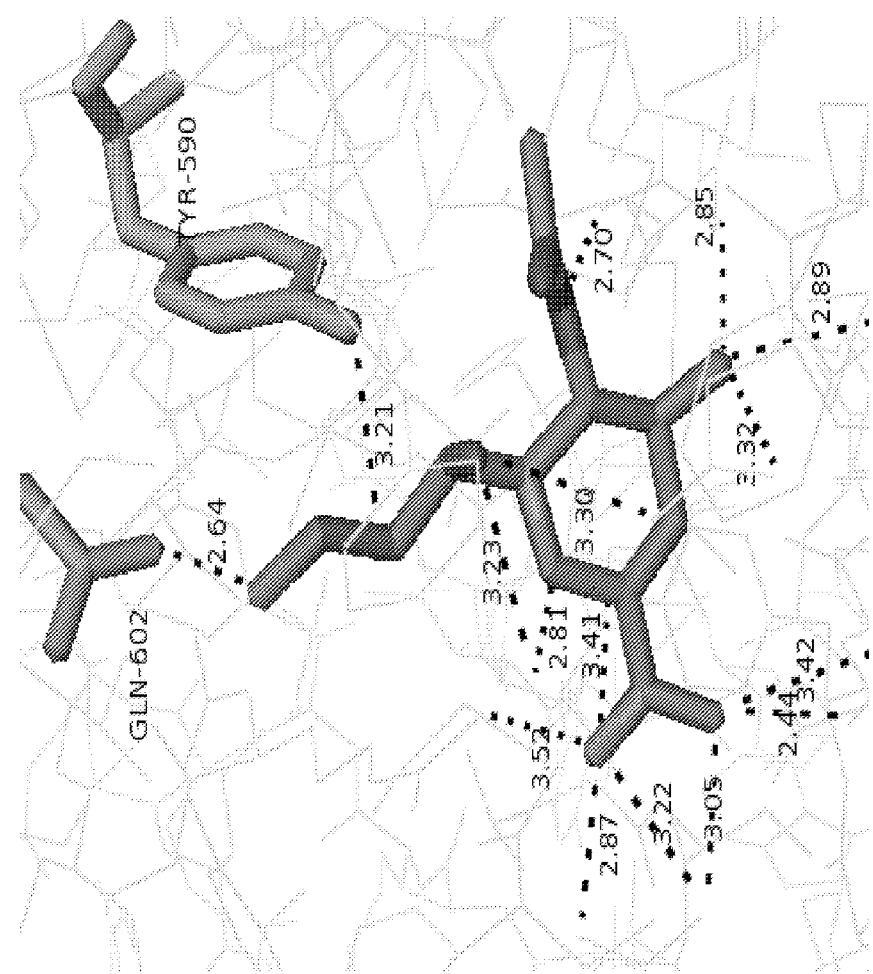
Figure 19C:
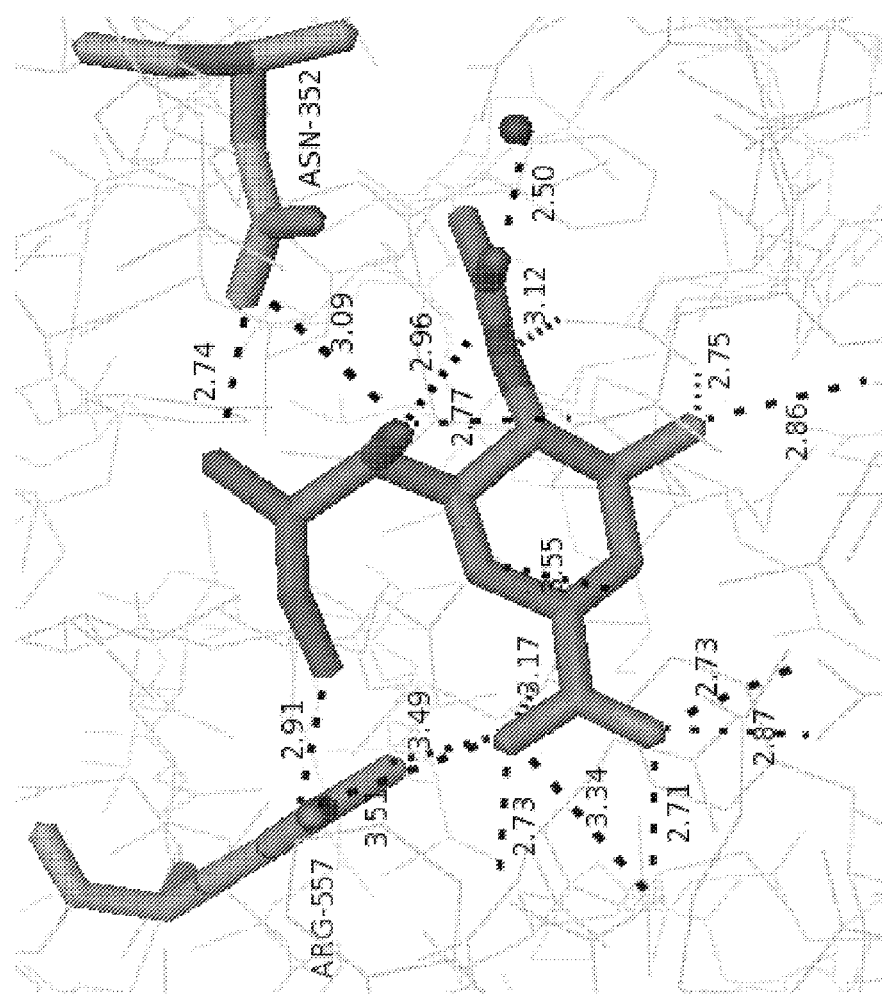
Figure 19D:
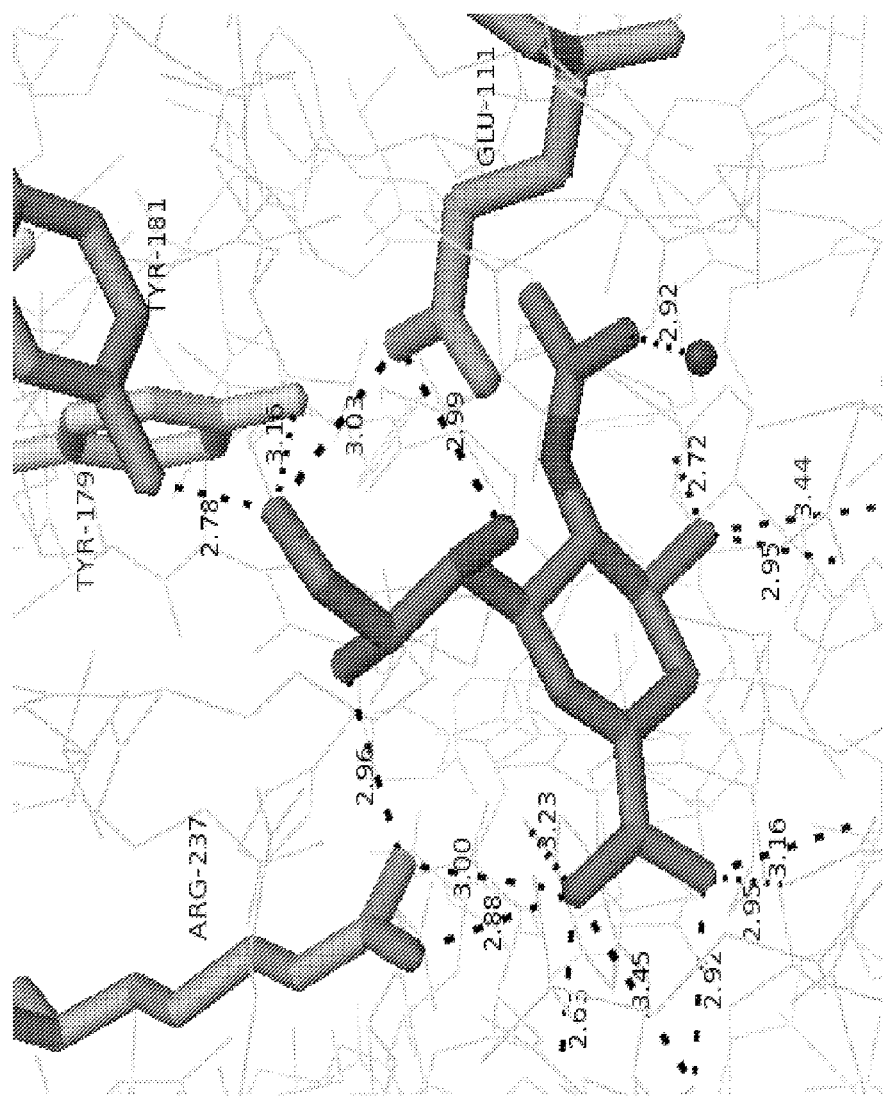

Referring now to FIG. 18, an overlay is shown of Zanamivir (carbons are shown in purple) bound to 18NA and Neu5Ac2en bound to CNanA (carbons are shown in green), NanB (carbons are shown in light blue), and NEU2 (carbons are shown in yellow). Zanamivir is a neuraminidase inhibitor used in the treatment and prophylaxis of Influenzavirus A and Influenzavirus B.

On the other hand, the C8-OH in Neu5Ac2en is separated from both bacterial sialidases and human NEU2 by a relatively big cavity, while the C8-OH in the Zanamivir, a strong inhibitor for the influenza virus neuraminidase, makes extensive contact with 18NA. The Neu5Ac2en derivatives with a C8-alkoxyl group may have improved inhibitory activity against *S. pneumoniae* NanA and NanB. This enhancement may not be selective, as we expect a similar impact for inhibition of human sialidase NEU2.

Referring now to FIG. 19, the interaction of sialidases and inhibitors is shown in panels: (A) catalytic domain of *S. pneumoniae* NanA (CNanA) with Neu5Ac2en; (B) *S. pneumoniae* NanB with Neu5Ac2en; (C) human NEU2 with Neu5Ac2en; and (D) 1918 influenza virus H1N1 neuraminidase (18NA) with Zanamivir.

In contrast, our modeling studies indicate that Neu5Ac2en analogs with an alkyl ether modification at C9-OH (FIG. 19) will have improved inhibitory activity and enhanced selectivity for *S. penumoniae* NanA and/or NanB and decreased inhibitory activity toward human NEU2. In addition, docking experiments (see Table 2, below) indicated that Neu5Ac2en derivatives 2, 3, 4, 5, and 7 may also have better inhibitory activity against NanA compared to non-modified Neu5Ac2en 1. In particular, compound 2 is predicted to improve binding to NanA, NanB and viral sialidase while reducing binding to human sialidase NEU2. More interestingly, compound 8 with a 9-O-ethyl group and an 8-O-methyl group on Neu5Ac2en is predicted to have equal binding to NanA and NanB but decreased binding to human NEU2 and viral 18NA (highlighted in italics and bold in Table 2). Compound 8 is a good candidate as a selective inhibitor for bacterial sialidases.

TABLE 2

Figure 20:
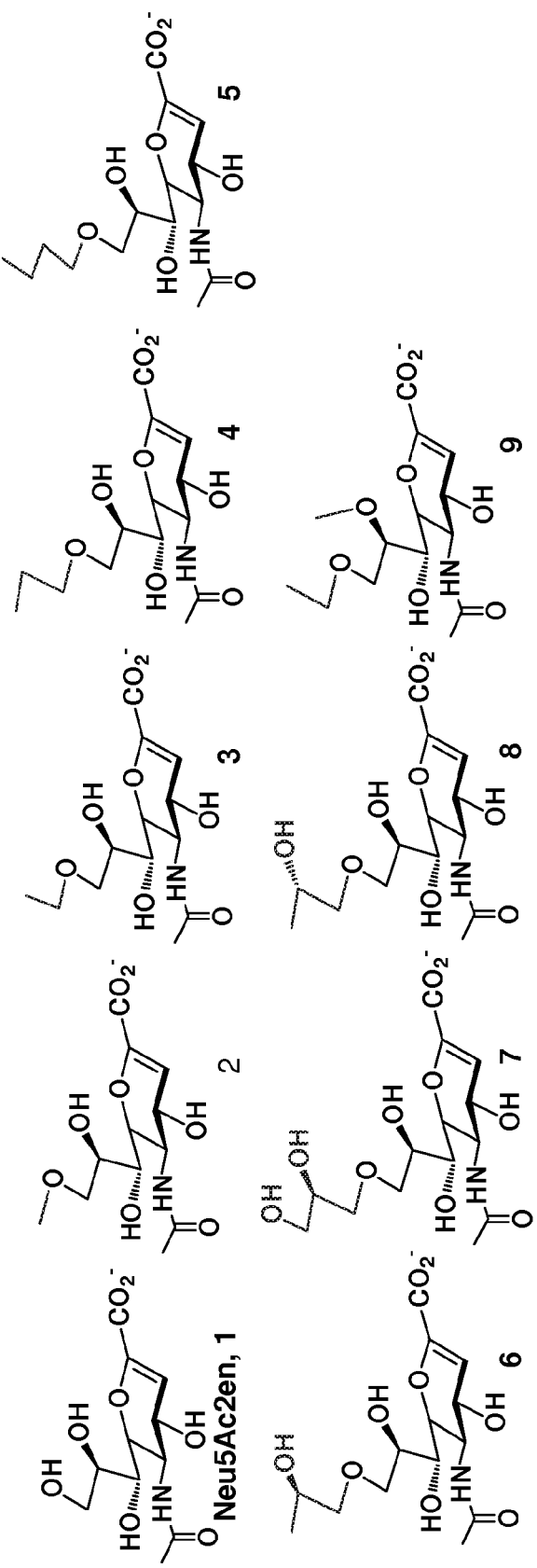
FIG. 20 depicts structures of Neu5Ac2en and its derivatives used as sialidase inhibitors.

Docking scores of Neu5Ac2en or its derivatives bind to CNanA, NanB, NEU2, or 18NA. The structures of compounds 1-9 (see FIG. 20) were drawn using Gaussview 3.09 and optimized with the Gaussian 03W. Protein binding sites were created with FRED Receptor 2.2.5 based on the inhibitor-bound protein crystal structures. The analogs were docked into the protein binding sites with FRED. The sum of three scoring functions [PLP, chemgauss3, and Oechemscore] is shown. The lower the score, the better the binding of the analog to the protein.

| Analogs | CNanA | NanB | NEU2 | 18NA |
| --- | --- | --- | --- | --- |
| 1 | −133 | −128 | −117 | −62 |
| 2 | −147 | −130 | −115 | −82 |
| 3 | −145 | −111 | −104 | −62 |
| 4 | −146 | −112 | −108 | −64 |
| 5 | −139 | −120 | −103 | −64 |
| 6 | −130 | −119 | −109 | −65 |
| 7 | −136 | −122 | −98 | −59 |
| 8 | −133 | −129 | −71 | −40 |
| 9 | −120 | −108 | −98 | −31 |

Compound 1 Neu5Ac2en together with C5-derivative Neu5Gc2en have been successfully synthesized using a novel chemoenzymatic method involving a sialic acid aldolase-catalyzed reaction. To test their predicted selectivity of inhibition against bacterial sialidases NanA and NanB, compounds 2-9 are synthesized similarly. Briefly, Neu5Ac and 8-O-methylneuraminic acid (Neu5Ac8OMe) prepared from N-acetylmannosamine (ManNAc) or 5-O-methyl ManNAc catalyzed by a sialic acid aldolase can be readily converted to 2,3-dehydro products using a reported method. Selective protection and deprotection of 2,3-dehydro compound following known procedures will afford a free C-9 primary hydroxyl group. Various alkyl groups are then installed on the free hydroxyl group at C-9 by reacting with alkyl bromides. Deacetylation and saponification will afford Neu5Ac2en derivatives 2-9. This chemoenzymatic synthetic approach can be used as a general approach to synthesize a diverse library of Neu5Ac2en derivatives with modifications at different carbons. The application of an aldolase in producing more complex nine-carbon monosaccharides from chemically modified six-carbon monosaccharides provides increased efficiency.

Since not all of the sialidase crystal structures are available, a focused random library of Neu5Ac2en and Neu5Gc2en derivatives can be synthesized using a similar sialic acid aldolase-catalyzed chemoenzymatic approach. This library includes Neu5Ac2en and Neu5Gc2en derivatives with modifications at C8-OH and/or carbon-5 with or without C9-OH modification. These compounds can be tested as potential inhibitors for *S. pneumoniae* NanA, NanB, and NanC as well as for other commercially available bacterial sialidases. The human sialidase NEU2 has been cloned and we have purified and unpurified avian and human influenza virus particles. The selectivity of the potential bacterial sialidase inhibitors is tested against these human and viral sialidases. The compounds selective for bacterial sialidases and with IC50 of less than 100 nM can be tested for their inhibition of digestion of CD24 in vitro and protection in vivo. The combination of protein crystal structure-based rational design and inhibitor screening based on a focused compound library provides potent inhibitors having enhanced inhibition and selectivity toward targeted bacterial sialidases.

FIG. 20 depicts structures of Neu5Ac2en and its derivatives 1-9 used as sialidase inhibitors.

Methods, uses, dosages and schedules of the present technology can include the following aspects. The compositions and methods can be administered to subjects suffering from tissue damage relating to drug-induced toxicity, for example, drug overdoses, alcoholism, alcohol poisoning, vascular ischemia, liver ischemia and reperfusion, heart ischemia and reperfusion, atherosclerosis, myocardial infarction, stroke, heart failure, fulminant hepatitis caused by viral infection or drugs, surgeries that resulted in tissue damage, angina and any dysregulated immune response in which immune mediators, HMGB1, heat shock proteins (HSP) HSP70, HSP90 or cellular RNA are detected in the patient at levels above normal range that are indicative with other clinical signs and symptoms to be related to tissue damage. Methods for determining levels of these tissue-damage related immune modulators in the patient are routinely performed by those of ordinary skill, for example, by immunological detection of the modulators in blood, urine, and tissue samples.

In some embodiments, the present technology provides methods for treating a patient having one or more diseases or disorders associated with drug-side effect or tissue-damage immune responses associated with immune dysregulation not involving bacterial or viral pathologies, comprising administering to the host or patient an efficacious amount of a pharmaceutical composition comprising one or more DAMP and/or PAMP dependent inhibitors. The inhibitor can be one or more of CD24 active molecules, for example, a CD24 agonist; CD24; CD24 fragment, variant, or derivative, including CD24Fc fusion proteins; HMBG1-binding protein, including binding protein to HMBG1 Box B; antagonist of HMGB1, for example, polyclonal, monoclonal, recombinant, chimeric, humanized scFv antibody and antibody fragments to full length HMGB1, fragments of HMGB1 and preferably antibodies that bind and suppress the activity of HMGB1 Box B and combinations thereof. Optionally, the composition can include one or more of immunosuppressive agents including TNF-$\alpha$ antibody (infliximab), a TNF-R-Fc fusion protein (etanercept), IL-1 (interleukin-1) receptor antagonist, IL-6 (interleukin-6) receptor antagonist or high doses of corticosteroids.

In some embodiments, a method includes the steps of identifying a patient having a tissue-damage disease with an elevated level of one or more immune mediators including, serum alanine transaminase (ALT), HMGB1, heat shock proteins (HSP) HSP70, HSP90 or cellular RNA. These levels can optionally be compared with levels of each suggestive of being in the normal range. Elevated levels of these immune mediators can also be corroborated with other clinical signs and symptoms related to dug-side effects, for example drug overdose and tissue damage. The patient found with elevated levels of one or more immune mediators can then be administered a safe and therapeutically effective dose of the present compositions described herein.

In some embodiments, compositions of the present technology that include multiple components can be collectively or independently formulated and co-administered or separately administered.

The pharmaceutical compositions of the present technology are suitable for use in a variety of drug delivery systems. Examples of suitable formulations for use in the present technology are found in Remington's Pharmaceutical Sciences (Mack Publishing Company, Philadelphia, Pa., 17th ed. (1985)), which is incorporated herein by reference. In addition, for a brief review of methods for drug delivery, see, Langer, Science 249:1527-1533 (1990), which is incorporated herein by reference.

The present technology provides pharmaceutical compositions which include isolated antibodies against full length HMGB1, fragments, motifs, or derivatives thereof. In some embodiments, the antibody suppresses the activity of HMGB1 stimulatory Box B. In some embodiments, the present technology provides pharmaceutical compositions comprising antibodies, including, polyclonal, monoclonal antibody, fragments, e.g. $Fab_2$, Fab', scFv, chimeric antibodies and recombinant antibodies that specifically bind to full length HMGB1, fragments, motifs, or derivatives thereof described herein. These antibodies find use in the therapeutic and diagnostic methods described herein.

An antibody against full length HMGB1, fragments, motifs, or derivatives thereof of the present technology may be any monoclonal or polyclonal antibody, as long as it can recognize at least part of the full length of HMGB1, and preferably the stimulatory Box B portion of HMGB1 and suppresses its activity, availability or expression. Antibodies can be produced by using a full length HMGB1, fragments, motifs, or derivatives or antigenic fragment thereof taught in the present technology as the antigen according to conventional antibody or antiserum preparation processes.

The present technology contemplates the use of both monoclonal and polyclonal antibodies that are pharmaceutically acceptable and having a risk/benefit ratio that is commensurate with standard pharmaceutical treatments used to treat dysfunctional immune responses related to drug side-effects and tissue-damage. Any suitable method may be used to generate the antibodies used in the methods and compositions of the present technology, including but not limited to, those disclosed herein. For example, for preparation of a monoclonal antibody, full length HMGB1, fragments, motifs, or derivatives thereof, as such, or together with a suitable carrier or diluent is administered to an animal (e.g., a mammal) under conditions that permit the production of antibodies. For enhancing the antibody production capability, complete or incomplete Freund's adjuvant may be administered. Normally, the full length HMGB1, fragments, motifs, or derivatives thereof can be administered once every 2 weeks to 6 weeks, in total, about 2 times to about 10 times to the animal used to produce the antibodies. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in the antiserum can be carried out, for example, by quantifying the amount of specific antibody binding to a labeled full length HMGB1, fragments, motifs, or derivatives thereof. The cell fusion can be carried out according to known methods, for example, the method described by Koehler and Milstein (Nature 256:495 (1975)). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used can be about 1:1 to about 20:1. PEG (preferably PEG 1000-PEG 6000) can be added in concentrations of about 10% to about 80%. Cell fusion can be carried out efficiently by incubating a mixture of both cells at about 20° C. to about 40° C., including about 30° C. to about 37° C. for about 1 minute to 10 minutes.

Various methods can be used for screening for a hybridoma producing the antibody (e.g., against a biomarker of the present technology). For example, a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the PRDX bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the PRDX bound to the solid phase.

Selection of the monoclonal antibody will be made based on their biological functions. For example, anti-Siglec 10 or anti-CD24 antibodies will be selected based on their ability to reduce production of inflammatory cytokines elicited by DAMPs. The methods can include stimulating a human myeloid cell line with HMGB1 in the presence or absence of different amounts of anti-CD24 or anti-siglec 10 mAbs, the cytokines will be measured at 6 hours after treatment. Those that show the maximal reduction of the cytokines will be selected for further testing in animal model of tissue injuries, as outlined in this application.

In another embodiment, anti-CD24 or anti-Siglec 10 mAbs can be selected based on the ability of the antibodies to stabilize the trimolecular complexes consisting of CD24, HMGB1, and Siglec 10. In brief, purified CD24Fc, Siglec 10 Fc, HMGB1 (1 µg/ml) will be incubated with different ranges of anti-CD24 or anti-Siglec 10 mAbs. The amount of complexes will be measured by co-immunoprecipitation as is known in the art.

Separation and purification of a monoclonal antibody can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from subjects. For example, a complex of an HMGB1 immunogen (an antigen of HMGB1) and a carrier protein is prepared and an animal is immunized by the complex according to the same manner as that described with respect to the above monoclonal antibody preparation. A material containing the antibody is recovered from the immunized animal and the antibody is separated and purified.

As to the complex of the HMGB1 immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to a hapten in a weight ratio of about 0.1 parts to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present technology. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The HMGB1 protein used herein as the immunogen is not limited to any particular type of HMGB1 immunogen. For example, any full length HMGB1 protein, fragments, motifs, or derivatives thereof. Preferably, an antigenic region of the HMGB1 stimulatory Box B the present technology can be used as the HMGB1 immunogen. Further, fragments of the HMGB1 protein may be used. Fragments may be obtained by any method including, but not limited to expressing a fragment of the HMGB1 gene, enzymatic processing of the protein, chemical synthesis, and the like.

While it is possible for the antibodies which are capable of binding to HMGB1 or can suppress the activity of HMGB1 to be administered in a pure or substantially pure form, it is preferable to present HMGB1 antibodies as a pharmaceutical composition, formulation or preparation, that is safe and therapeutically effective in reducing any indicator of a pathologic immune response associated with a drug-side effect, cellular necrosis or damage as a result of a chemical injury, e.g. aspirin, acetaminophen, narcotics, alcohol and toxins (bacterial, plant, insect, vertebrate and the like).

In addition to antibodies to HMGB1, the formulations of the present technology, both for veterinary and for human use, can comprise a DAMP dependent inhibitor which can include one or more of (a) CD24 active molecules, for example, a CD 24 agonist such as CD24; CD24 fragments, variants and derivatives, including CD24Fc fusion proteins; (b) Siglec-10 active molecules, for example, a Siglec-10 agonist such as Siglec-10; Siglec-10 fragments, variants, and derivatives, including Siglec-10Fc fusion proteins; (c) HMBG1-binding proteins, including binding proteins to HMBG1 Box B; antagonists of HMGB1, for example, polyclonal, monoclonal, recombinant, chimeric, humanized scFv antibodies and antibody fragments to full length HMGB1, fragments of HMGB1 and antibodies that bind and suppress the activity of HMGB1 Box B; (d) sialidase inhibitors such as Neu5Ac2en and/or Neu5Gc2en, and derivatives thereof; and combinations of (a), (b), (c), and (d). Optionally, the composition can also include one or more immunosuppressive agents including TNF-α antibody (infliximab), a TNF-R-Fc fusion protein (etanercept), IL-1 (interleukin-1) receptor antagonist, IL-6 (interleukin-6) receptor antagonist or high doses of corticosteroids as described above, together with one or more pharmaceutically acceptable carriers. The carrier(s) must be "acceptable" in the sense of being compatible with the other ingredients of the formulation and not toxic or allergenic to the recipient thereof. The formulations may conveniently be presented in unit dosage form and may be prepared by any method well-known in the pharmaceutical art.

The compositions of the present technology can be formulated for parenteral, topical, oral or local administration. In certain aspects, the compositions are administered parenterally, (e.g., intravenously, subcutaneously, intradermally, or intramuscularly). In some embodiments, the technology provides compositions for parenteral administration which comprises a DAMP and/or PAMP dependent inhibitor and optionally an immunosuppressive agent as described above, dissolved or suspended in an acceptable pharmaceutical excipient or carrier, preferably an aqueous carrier. A variety of aqueous carriers may be used including, for example, water, buffered water, 0.4% saline, 0.3% glycine, hyaluronic acid and the like. These compositions may be sterilized by conventional, well-known sterilization techniques or, they may be sterile filtered. The resulting aqueous solutions may be packaged for use as is or lyophilized, the lyophilized preparation being combined with a sterile solution prior to administration.

The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc. One or more stabilizers can be added to the pharmaceutical compositions contemplated herein. Illustrative stabilizers are poly-ethylene glycol, proteins, polysaccharides, amino acids, inorganic acids, and organic acids which may be used either on their own or as admixtures. These stabilizers are preferably incorporated in an amount of 0.11-10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of 0.1-3.0 osmoles, preferably in the range of 0.8-1.2. The pH of the aqueous solution is adjusted to be within the range of 5.0-9.0, preferably within the range of 6-8. In formulating the immunogen of the present technology, one or more anti-adsorption agents may be used.

For solid formulations, a DAMP and/or PAMP dependent inhibitor can be admixed with conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%. In powders, the carrier is a finely divided solid that is in a mixture with the finely divided active component. In tablets, the active component is mixed with the carrier having the necessary binding properties in suitable proportions and compacted in the shape and size desired.

Powders and tablets preferably contain from 5% to 95% of the active DAMP dependent inhibitor. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active DAMP dependent inhibitor with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For aerosol administration, the DAMP dependent inhibitor and optionally an immunosuppressive agent are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, (e.g., lecithin for intranasal delivery).

The pharmaceutical composition is preferably in unit dosage form. In such form the pharmaceutical composition is subdivided into unit doses containing appropriate quantities of the DAMP dependent inhibitor. The unit dosage form can be a packaged preparation, the package containing discrete quantities of preparation, such as blisters, packeted tablets, capsules, and powders and/or beads in vials, bags, sachets or ampoules. Also, the unit dosage form can be a capsule, tablet, cachet, or lozenge itself, or it can be the appropriate number of any of these in packaged form.

The quantity of active components in a unit dose preparation may be varied or adjusted from 0.01 mg to 10000 mg, preferably 0.1 mg to 5000 mg according to the particular application and the potency of the DAMP dependent inhibitor. The composition can, if desired, also contain other compatible therapeutic agents. In therapeutic use especially for the treatment of drug-side effects or liver or coronary toxicity, ischemia or reperfusion conditions, the DAMP dependent inhibitors utilized in the pharmaceutical method of the present technology can be administered at the initial dosage ranging from about 0.00001 mg/kg to about 500 mg/kg daily. A daily dose range of about 0.0001 mg/kg to about 150 mg/kg is preferred. Most preferably, the daily dose range is comprised between 0.001 mg/kg and 100 mg/kg, especially between 0.01 mg/kg and 25 mg/kg. The dosages, however, may be varied depending upon the requirements of the patient, the severity of the condition being treated, and the compound being employed.

Determination of the proper dosage for a particular situation is within the skill of the practitioner. Generally, treatment is initiated with smaller dosages that are less than the optimum dose of the compound. Thereafter, the dosage is titrated upwardly by small increments until the optimum effect under circumstances is reached. For convenience, the total daily dosage may be divided and administered in portions during the day, if desired. In therapeutic applications, the DAMP and/or PAMP dependent inhibitor and optional immunosuppressive agents of the present technology are administered to a patient in a combination amount sufficient to elicit a response. An amount adequate to accomplish this is defined as "therapeutically effective combination dose." The methods include the administration of the DAMP and/or PAMP dependent inhibitor with an optional immunosuppressive agent wherein the two components are delivered in a simultaneous manner, in combination therapy wherein the one or more DAMP and/or PAMP dependent inhibitors are administered first, followed by the immunosuppressive agent, as well as wherein the optional immunosuppressive agent is delivered first followed by the DAMP and/or PAMP dependent inhibitor.

The method of the present technology also includes administration of a composition wherein the DAMP and/or PAMP dependent inhibitor strengthens association between CD24 and Siglec-10. The method of the present technology also includes administration of a composition wherein the DAMP and/or PAMP dependent inhibitor increases sialidation of CD24 to enhance the CD24-Siglec-10 interaction. The methods of the present technology also include administration of a composition wherein the DAMP and/or PAMP dependent inhibitor increases the interaction between CD24 and Siglec-10. The method of the present technology also includes administration of a pharmaceutical composition wherein the DAMP dependent inhibitor targets other members of the Siglec family that interact with CD24.

The embodiments and the examples described herein are exemplary and not intended to be limiting in describing the full scope of apparatus, compositions, systems, and methods of the present technology. Equivalent changes, modifications and variations of some embodiments, materials, compositions and methods can be made within the scope of the present technology, with substantially similar results.

What is claimed is:

1. A method for treating inflammation from septic injuries in a subject comprising administering to the subject a composition comprising a sialidase inhibitor and a CD24-Fc fusion protein.

2. A method according to claim 1, further comprising administering a Siglec-10 agonist to the subject, wherein the Siglec-10 agonist comprises an anti-Siglec-10 antibody.

3. The method of claim 1, wherein the sialidase inhibitor comprises Neu5Ac2en or a derivative thereof.

4. The method of claim 1, wherein the sialidase inhibitor comprises Neu5Gc2en or a derivative thereof.

5. The method of claim 1, wherein the sialidase inhibitor comprises Neu5Ac2en and Neu5Gc2en.

6. The method of claim 1, wherein the administering includes parenteral administration.

7. The method of claim 1, wherein the sialidase inhibitor is selected from compounds 1-9:

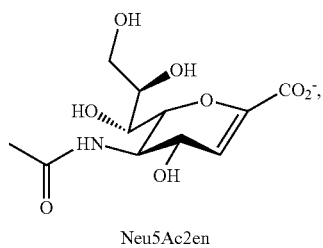

Neu5Ac2en

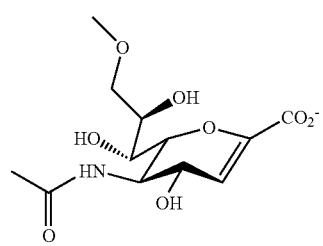

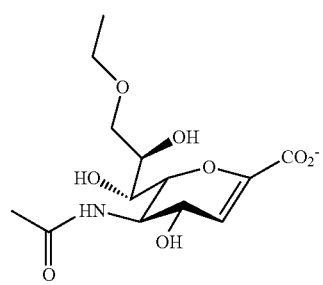

-continued

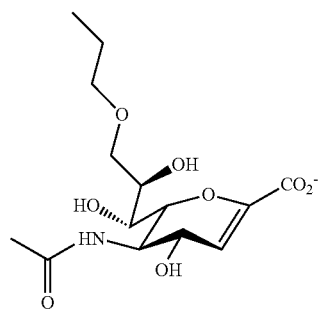

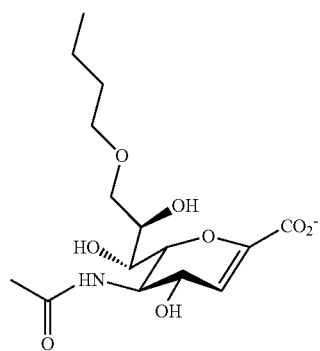

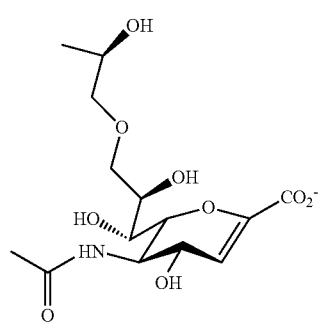

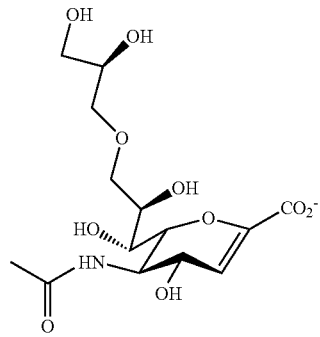

-continued
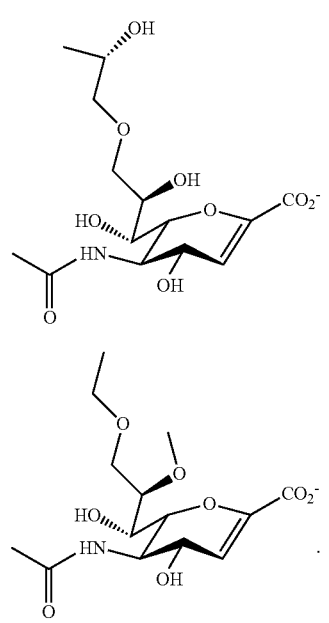
8. A method according to claim 7, wherein the sialidase inhibitor comprises compound 9.
* * * * *